United States Patent

Hamprecht et al.

[11] Patent Number: 5,591,694
[45] Date of Patent: Jan. 7, 1997

[54] HERBICIDAL SULFONYLUREAS

[75] Inventors: Gerhard Hamprecht, Weinheim; Horst Mayer, Ludwigshafen; Karl-Otto Westphalen, Speyer; Helmut Walter, Obrigheim; Matthias Gerber, Mutterstadt; Uwe Kardorff, Mannheim, all of Germany

[73] Assignee: BASF Aktiengesellschaft, Ludwigshafen, Germany

[21] Appl. No.: 199,284

[22] PCT Filed: Sep. 25, 1992

[86] PCT No.: PCT/EP92/01879

§ 371 Date: Feb. 28, 1994

§ 102(e) Date: Feb. 28, 1994

[87] PCT Pub. No.: WO93/05048

PCT Pub. Date: Mar. 18, 1993

[30] Foreign Application Priority Data

Aug. 28, 1991 [DE] Germany .................. 41 28 441.0

[51] Int. Cl.$^6$ ............... C07D 239/52; C07D 239/69; A01N 43/54
[52] U.S. Cl. ....................... 504/214; 544/321
[58] Field of Search ............ 504/214; 544/321, 544/323

[56] References Cited

U.S. PATENT DOCUMENTS 4,547,215  10/1985  Wolf ........................ 544/321
5,188,657   2/1993  Hamprecht ................ 504/212
5,276,007   1/1994  Hamprecht et al. ....... 504/214

FOREIGN PATENT DOCUMENTS 072347  2/1983  European Pat. Off. .
084020  7/1983  European Pat. Off. .
169815  1/1986  European Pat. Off. .
446743  9/1991  European Pat. Off. .
469460  2/1992  European Pat. Off. .

Primary Examiner—John M. Ford
Attorney, Agent, or Firm—Keil & Weinkauf

[57] ABSTRACT

Substituted sulfonylureas of the formula I

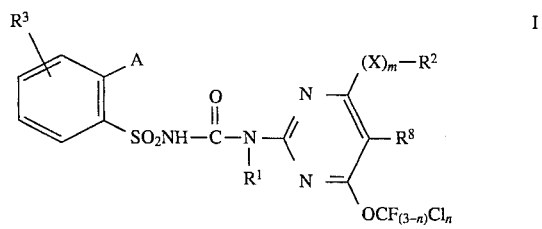

wherein, inter alia, n and m are each 0 or 1;

X is O, S or N—$R^4$, where $R^4$ is hydrogen or alkyl;

A is $NO_2$, $NH_2$, OH, CN, SCN, $S(O)_oR^5$, $SO_2NR^6R^7$ or $ER^7$;

and environmentally compatible salts of the compounds. The disclosure is also directed to a process for preparing the compounds, to intermediates for the preparation of the compounds and to the use of the compounds as herbicides.

6 Claims, No Drawings

HERBICIDAL SULFONYLUREAS

This application is a 371 of PCT/EP92/01879 filed Sep. 25, 1992, and published as WO93/05048 Mar. 18, 1993.

The present invention relates to substituted sulfonylureas of the formula I

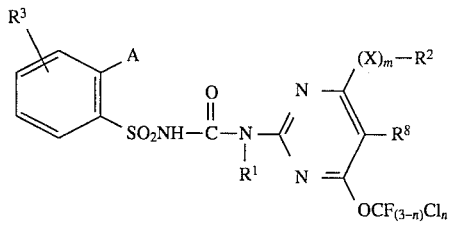

where n and m are each 0 or 1;

$R^1$ is hydrogen, $C_1$–$C_4$-alkyl, $C_3$–$C_6$-alkenyl or $C_3$–$C_6$-alkynyl;

$R^2$ is halogen or trifluoromethyl when m is 0 or $C_1$–$C_4$-alkyl, $C_3$–$C_6$-alkenyl or $C_3$–$C_6$-alkynyl when m is 1 or trifluoro- or chlorodifluoromethyl when X is O or S and m is 1;

X is O, S or N—$R^4$, where $R^4$ is hydrogen or $C_1$–$C_4$-alkyl;

$R^3$ is hydrogen, halogen, $C_1$–$C_4$-alkyl, $C_1$–$C_4$-haloalkyl, $C_1$–$C_4$-alkoxy or $C_1$–$C_4$-haloalkoxy;

A is $NO_2$, $NH_2$, OH, CN, SCN, $S(O)_o R^5$, $SO_2NR^6R^7$, a group $ER^7$, where E is O, S or $NR^9$,

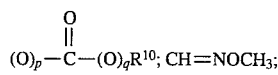

$C_1$–$C_4$-alkyl which is unsubstituted or mono-, di- or trisubstituted by methoxy, ethoxy, $SO_2CH_3$, cyano, thiocyanato or $SCH_3$, or $C_2$–$C_4$-alkenyl which is unsubstituted or mono-, di- or trisubstituted by halogen, nitro or cyano;

$R^5$ is $C_1$–$C_6$-alkyl which may carry from one to three of the following radicals: halogen, $C_1$–$C_4$-alkoxy, $C_1$–$C_4$-haloalkoxy, $C_1$–$C_4$-alkoxy-$C_1$- or $C_2$-alkoxy, $C_3$–$C_7$-cycloalkyl and/or phenyl; $C_5$–$C_7$-cycloalkyl which may carry from one to three $C_1$–$C_4$-alkyl groups; $C_2$–$C_6$-alkenyl or $C_3$–$C_6$-alkynyl; $R^6$ is hydrogen, $C_1$- or $C_2$-alkoxy or $C_1$–$C_6$-alkyl, or, together with $R^7$, forms a $C_4$–$C_6$-alkylene chain in which a methylene group may be replaced with an oxygen atom or a $C_1$–$C_4$-alkylimino group;

$R^7$ is $C_1$–$C_4$-alkyl, $C_2$–$C_4$-alkenyl or $C_3$- or $C_4$-alkynyl, it being possible for the stated radicals to carry a further one to four halogen or $C_1$–$C_4$-alkoxy radicals, or is $C_3$–$C_6$-cycloalkyl, or where E is $NR^9$, is furthermore methylsulfonyl, trifluoromethylsulfonyl, ethylsulfonyl, acetyl which may carry one to three halogen atoms, or methoxycarbonyl, dimethylcarbamoyl or dimethylsulfamoyl;

o is 0, 1 or 2;

p and q are 0 and/or 1, and, where p is 0, q is likewise 0, and $R^8$ is hydrogen or halogen;

$R^9$ is hydrogen, methyl or ethyl;

$R^{10}$ is $C_1$–$C_3$-alkyl, $C_1$–$C_3$-haloalkyl, $C_1$- or $C_2$-alkoxy-$C_1$- or $C_2$-alkyl, $C_2$–$C_4$-alkenyl, $C_3$–$C_6$-cycloalkyl or $C_2$- or $C_3$-haloalkenyl, or, where p is 1 and q is 0, is furthermore $C_1$–$C_3$-alkylamino or di-($C_1$- or $C_2$-alkyl)-amino, and environmentally compatible salts thereof.

The present invention furthermore relates to a process for the preparation of the compounds I and to their use as herbicides and intermediates for the preparation of the sulfonylureas I.

U.S. Pat. No. 4,547,215 discloses, as herbicides, various sulfonylureas which are substituted in the pyrimidine moiety by chlorine. EP-A-72 347, 84 020 and 169 815 describe sulfonylureas which are substituted in the pyrimidine moiety by difluoromethoxy or bromodifluoromethoxy. However, these compounds have unsatisfactory selectivity with respect to weeds. Sulfonylureas with different substitution patterns on the phenyl radical are disclosed in the prior Applications EP-A-446 743 and EP-A-469 460.

It is an object of the present invention to provide novel compounds from the class consisting of the sulfonylpyrimidylureas, having improved herbicidal properties.

We have found that this object is achieved by the sulfonylureas defined at the outset.

We have furthermore found that the compounds of the formula I and the alkali and alkaline earth metal salts thereof have good selectivity with respect to weeds in crops such as cereal and corn.

we have also found chemically unique processes for the preparation of the compounds I. In comparison with the prior art, the sulfonylureas I can unexpectedly be prepared in regioselective form and in high yield and purity starting from substituted 2-amino-4-fluoroalkoxy-6-pyrimidines of the general formula IIIa

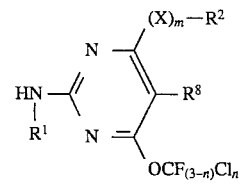

where m is 1 and n is 0 or 1;

$R^1$ is hydrogen, $C_1$–$C_4$-alkyl, $C_3$–$C_6$-alkenyl or $C_3$–$C_6$-alkynyl;

$R^2$ is $C_1$–$C_4$-alkyl, $C_3$–$C_6$-alkenyl or $C_3$–$C_6$-alkynyl;

$R^8$ is hydrogen or halogen;

X is O, S or N—$R^4$ and $R^4$ is hydrogen or $C_1$–$C_4$-alkyl.

For the preparation of compounds which are halogen-substituted in the pyrimidine moiety ($R^2$=Hal, m=0), correspondingly substituted 2-amino-4-fluoroalkoxy-6-halopyrimidines of the structure IIIb are used as starting materials (cf. Scheme 2), the preparation of such pyrimidines being the subject of German Application P 40 07 316 (O.Z. 0050/41451). The pyrimidine intermediates in which m is 0 and $R^2$ is trifluoromethyl are obtained in a similar manner according to Scheme 3.

The novel sulfonylureas of the formula I are obtainable by methods A, B and C described in Scheme 1:

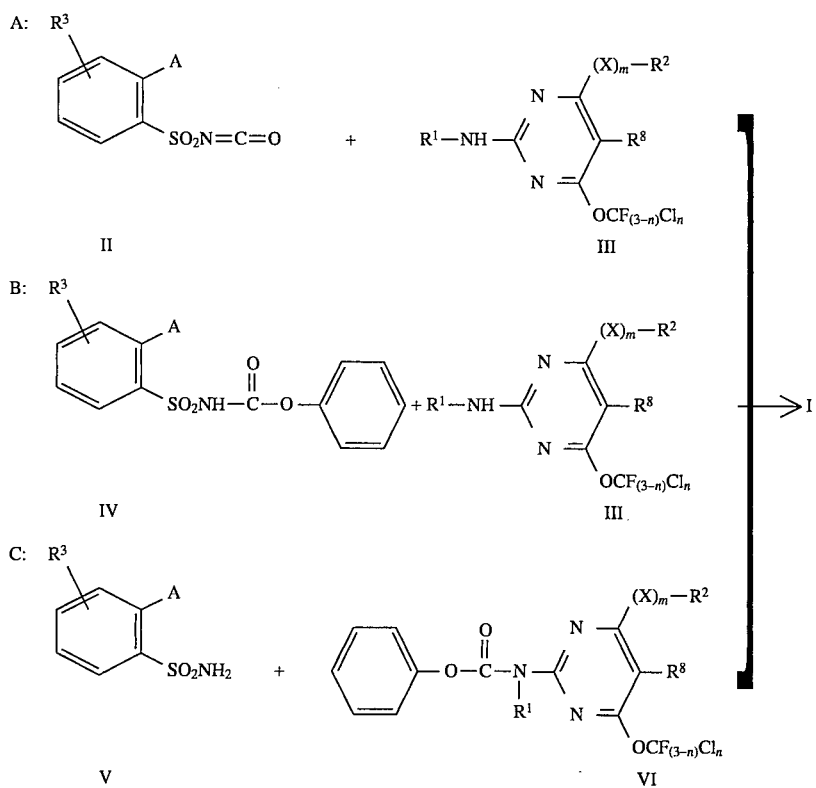

Embodiment A

A sulfonyl isocyanate II is reacted in a conventional manner (EP-A-162 723) with about a stoichiometric amount of 2-aminopyrimidine derivative III in an inert organic solvent at from 0° to 120° C., preferably from 10° to 100° C. The reaction can be carried out at atmospheric or super-atmospheric pressure (up to 50 bar), preferably at from 1 to 5 bar, continuously or batchwise. Suitable solvents are stated in the abovementioned literature.

Embodiment B:

A corresponding sulfonylcarbamate of the formula IV is reacted in a conventional manner (EP-A-162 723) with a 2-aminopyrimidine derivative in an inert organic solvent at from 0° to 120° C., preferably from 10° to 100° C. Bases, such as tertiary amines, may be added here, with the result that the reaction is accelerated and the product quality improved.

Suitable bases for this purpose are, for example, tertiary amines, such as pyridine, the picolines, 2,4- and 2,6-lutidine, 2,4,6-collidine, p-dimethylaminopyridine, 1,4-diaza[2.2.2]bicyclooctane (DABCO) and 1,8-diazabicyclo[5.4.0]undec-7-ene.

Advantageously used solvents are those stated in the literature and/or halohydrocarbons, such as dichloromethane and chlorobenzene, ethers, such as diethyl ether, tetrahydrofuran and dioxane, acetonitrile, dimethylformamide and/or ethyl acetate, in an amount of from 100 to 4,000, preferably from 1,000 to 2,000, % by weight, based on the starting materials II, IV and V.

For the preparation of the novel compounds, the 2-aminopyrimidine intermediates III are obtainable in the following advantageous manner:

Scheme 2

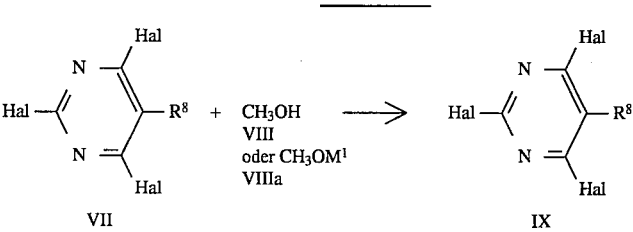

-continued
Scheme 2

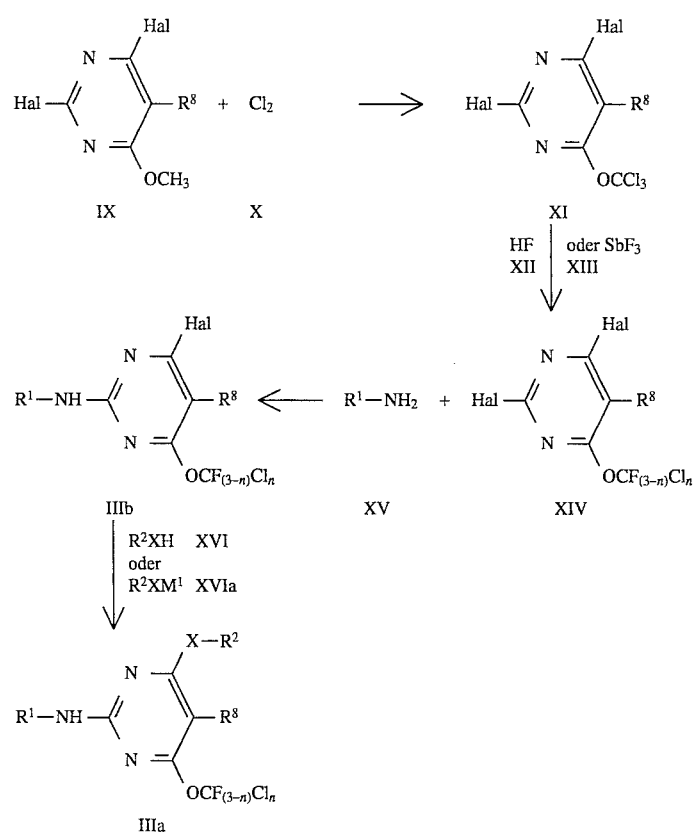

2-Amino-6-trifluoromethylpyrimidine derivatives IIIc are obtained in a corresponding manner if, instead of the 2,4,6-trihalo compounds VII, the corresponding 2,4-dihalo-6-trichloromethylpyrimidines are reacted according to Scheme 3 (cf. Examples I.1, I.6 and I.12).

Scheme 3

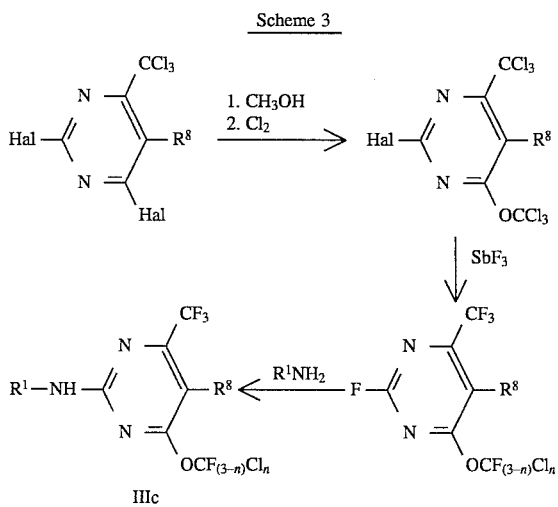

The intermediates IIId

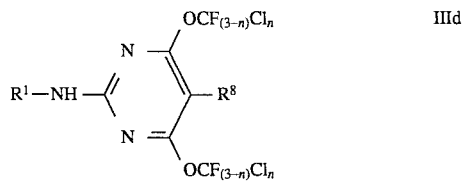

are obtained starting from the intermediates XIV in Scheme 2 and substituting the halogen atom in the 4-position by the reaction sequence described in Scheme 3 (1. $CH_3OH$, 2. $Cl_2$, 3. $SbF_3$) and then reacting with $R^1NH_2$.

According to Scheme 2, for example, 2,4,6-trihalopyrimidine VII, disclosed in J. Med. Chem. 6 (1963), 688 or commercially available, can be reacted in an aprotic polar solvent a) with methanol VIII in the presence or absence of a base or b) with a methylate VIIIa in the presence of methanol VIII at from −40° to 120° C. to give the methoxypyrimidine IX. These reactions can be carried out under atmospheric or superatmospheric pressure (from 1 to 10, preferably from 1 to 5, bar), continuously or batchwise.

In the formula VII, Hal is fluorine, chlorine or bromine.

In the formula VIIIa, $M^1$ is an alkali metal cation, such as a lithium, sodium or potassium cation, or one equivalent of an alkaline earth metal cation, such as a magnesium, calcium or barium cation.

The following solvents are suitable for the reaction of the trihalopyrimidine with methanol VIII: Ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, chlorohydrocarbons, such as 1,1,2,2-tetrachloroethane, 1,1-dichloroethylene, chlorobenzene, 1,2-dichlorobenzene and 1-chloronaphthalene, and corresponding mixtures.

Advantageously, the solvent used in an amount of from 100 to 2,000, preferably from 500 to 1,500, % by weight, based on the starting material VII.

However, the reaction of the starting materials VII with VIII is advantageously carried out directly in the excess of methanol VIII as a solvent. If necessary, an alkali methylate VIIIa is added, in an equivalent amount or in an amount of up to 5%, based on the starting material VII, greater than or less than the stoichiometric amount, to a suspension of the starting material VII in from 5 to 20 times the amount by weight of alcohol VIII as a solvent, based on the starting material VII, in the course of not more than one hour at from −20° to 80° C. To end the reaction, stirring is then carried out for a further ½ hour to 8 hours at from 0° to 120° C., preferably from 0° to 100° C.

The working up methods conventionally used for this purpose in the literature, such as working up by distillation or chromatography, can be used for isolating the methoxypyrimidines.

The chlorination of methoxypyrimidine IX with chlorine X to give the trichloromethoxypyrimidine XI is carried out, for example, at from 60° to 180° C.

Suitable chlorinating agents are elemental chlorine or chlorine donors, such as sulfuryl chloride or phosphorus pentachloride. Chlorine can also be prepared in situ by oxidizing hydrochloric acid, for example with manganese dioxide or hydrogen peroxide, or by anodic chlorination.

The reaction can be carried out in the presence of an inert solvent, for example a chlorohydrocarbon, such as chloroform, carbon tetrachloride, chlorobenzene, 1,2-, 1,3- or 1,4-dichlorobenzene, a nitrile, such as acetonitrile, propionitrile, a nitro compound, such as nitrobenzene, a carboxylic acid such as acetic acid or propionic acid, an anhydride, such as acetic anhydride, an acyl chloride, such as chloroacetyl chloride, α-chloropropionyl chloride or α,α-dichloropropionyl chloride, an inorganic acid halide, such as phosphorus trichloride or phosphorus oxychloride, or preferably in the absence of a solvent, in the melt of the starting material IX.

If necessary, the reaction can be accelerated by adding a free radical initiator; suitable initiation of this type is exposure to light, preferably UV light, or the addition of α,α'-azobisisobutyronitrile, advantageously in an amount of from 0.2 to 7 mol %, based on the starting material IX. The reaction can also be accelerated by adding a catalyst. Suitable catalysts are phosphorus pentachloride, advantageously in an amount of from 0.5 to 7 mol %, based on the starting material IX. In this case, the starting material IX is initially taken together with the catalyst and the chlorination is then begun. Instead of the phosphorus pentachloride, a starting component which forms this under the reaction conditions, for example phosphorus trichloride or yellow phosphorus, may also be added and chlorination then begun.

The starting material IX can be reacted with chlorine in a virtually stoichiometric amount or, preferably, in excess, advantageously with from 3.1 to 11, in particular from 3.3 to 5, mol of $Cl_2$ per equivalent of methoxy in the starting material IX. The reaction can be carried out at from 60° to 180° C., advantageously at from 100° to 150° C., under atmospheric or superatmospheric pressure, continuously or batchwise.

Chlorination is effected at 1 bar, from 3.3 to 5 mol, based on one equivalent of methoxy in the starting material IX, of chlorine gas are advantageously used, corresponding to a chlorine conversion of from 91 to 60%. Using a suitable measure in terms of apparatus, for example by using moderate superatmospheric pressure, advantageously from 1 to 10 bar, or by employing a bubble column, it is possible to increase the chlorine conversion. The chlorine gas is advantageously allowed to come into contact with the organic phase for as long as possible, for example by vigorously stirring said phase or making it necessary for the chlorine gas to pass through a thick layer of the organic phase.

The reaction time is in general from about 0.5 to 12 hours.

In a preferred embodiment of the process, the required amount of chlorine gas is passed into the liquid starting material IX in the course of from 0.5 to 12, preferably from 1 to 10, hours with thorough stirring, the process being started at from 60° to 80° C. and this temperature being increased continuously, if necessary utilizing the exothermic nature of the reaction, so that toward the end the reaction is carried out at from 100° to 150° C. In the case of larger reaction batches, the exothermic nature is taken into account by external cooling or by suitable metering of the amount of chlorine; once the reaction abates, the cooling bath is removed and if necessary further heating may be carried out.

Working up and isolation of the end products can be detected in a conventional manner. For example, residues of hydrogen chloride, chlorine or catalyst can be removed from the hot organic phase by means of an inert gas; a crude product which is already very pure remains behind in high yield. It can be further purified by distillation or chromatography, or used directly for further reactions.

The reaction of the trichloromethoxypyrimidine XI with a halogen-exchanging agent is carried out, for example, at from 0° to 170° C.

A suitable halogen-exchanging agent is antimony trifluoride in the presence or absence of a catalytic amount of an antimony(V) salt, e.g. antimony(V) chloride, or hydrogen fluoride.

Advantageously, an excess of from 1 to 200, preferably from 5 to 20, mol % of antimony trifluoride is used per equivalent of trichloromethyl. The catalytic amount of antimony(V) salt is from 1 to 20, preferably from 5 to 18, mol % per equivalent of trichloromethyl. The starting material XI is preferably metered at from 90° to 130° C. into the mixture of the halogen-exchanging agent and the mixture is then heated for from 10 to about 120 minutes at from 140° to 170° C. Working up is then effected by distillation.

However, the reaction can also be carried out continuously by adding the starting material XI at from 140° to 170° C. in the course of from 10 to about 120 minutes and simultaneously distilling off the resulting low boiling end product XIV under reduced pressure. Traces of entrained antimony salts can be eliminated by extraction with concentrated hydrochloric acid.

If the reaction is carried out without catalysis by antimony(V) salts or only small amounts, for example 0.2 to 1 mol %, are used and the amount of antimony trifluoride reduced to 60–90 mol % per equivalent of trichloromethyl, the halogen exchange stops at the chlorodifluoromethoxy stage.

The halogen exchange can also be carried out using hydrogen fluoride at from 0° to 170° C., preferably from 40° to 120° C., instead of antimony trifluoride. For this purpose, an excess of from 300 to 700, preferably from 350 to 400, mol % of hydrogen fluoride per equivalent of trichloromethyl is added to the starting material XI in an autoclave, and the mixture is stirred for from 10 minutes to about 10 hours. After the pressure has been let down and volatile components removed, working up is effected as described above.

The reaction of the fluoromethoxypyrimidine XIV with an amine XV is carried out, for example, at from −80° to 40° C.

In the formula XV, $R^1$ is, for example, hydrogen, $C_1$–$C_4$-alkyl, such as methyl, ethyl, n-propyl, isopropyl, n-butyl, sec-butyl, isobutyl or tert-butyl, $C_3$- or $C_4$-alkenyl, such as 2-propenyl, 2-methylethenyl, 2-butenyl, 3-butenyl, 1-methyl-2-propenyl or 2-methyl-2-propenyl, or $C_3$- or $C_4$-alkynyl, such as propargyl, 2-butynyl, 3-butynyl or 1-methyl-2-propynyl.

Among the amines which may be used, the following are mentioned: ammonia, methylamine, ethylamine, n-propylamine, isopropylamine, n-butylamine, isobutylamine, sec-butylamine, tert-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine.

The 2,6-dihalopyrimidines XIV can be reacted with the amines XV in an aprotic polar solvent at from −80° to 40° C., either the amine XV being used in excess or an organic auxiliary base being employed.

For the reaction of the 2,6-dihalopyrimidine XIV with the amine XV, examples of suitable solvents are the following: Ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

Advantageously, the solvent is used in an amount of from 100 to 2,000, preferably from 400 to 1,200, % by weight, based on the starting material XIV.

From 1.8 to 2.5, in particular from 1.95 to 2.2, mol equivalent, based on the starting material. XIV, of the amine XV are advantageously added in the course of from 0.5 to 2 hours to a mixture of starting material XIV in one of the abovementioned solvents at from −80° to 40° C., preferably from −70° to 25° C., and the mixture is stirred for up to 3 hours until the reaction is complete and is then allowed to warm up to 25° C. for working up.

If only about a stoichiometric amount of the amine XV is used, from 0.9 to 1.1 equivalents, based on the starting material XIV, of an organic auxiliary base are advantageously employed. Suitable auxiliary bases are organic bases, such as trimethylamine, triethylamine, N-ethyldiisopropylamine, triisopropylamine, N,N-dimethylaniline, N,N-dimethylcyclohexylamine, N-methylpyrrolidine, pyridine, quinoline, α,β- and γ-picoline, 2,4- and 2,6-lutidine and triethylenediamine.

The reaction can be carried out under atmospheric or superatmospheric pressure, continuously or batchwise.

For working up, the reaction mixture is extracted with water to remove the salts, and the organic phase is dried and is purified, for example by chromatography. However, the organic phase may also be directly evaporated down and the residue stirred with a solvent.

The novel 2-amino-4-fluoroalkoxypyrimidines of the formula IIIa are advantageously obtained by a method in which a 2-amino-4-fluoroalkoxy-6-halopyrimidine of the formula IIIb

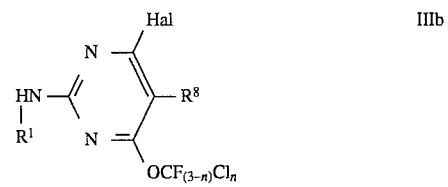

where Hal is fluorine, chlorine or bromine and $R^1$, $R^8$ and n have the abovementioned meanings, is reacted with a nucleophile of the formula XVI

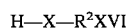

where X and $R^2$ have the abovementioned meanings, or a salt thereof.

Where 2-amino-4-fluoro-6-trifluoromethoxypyrimidine and methylamine is used, the reaction can be described by the following equation:

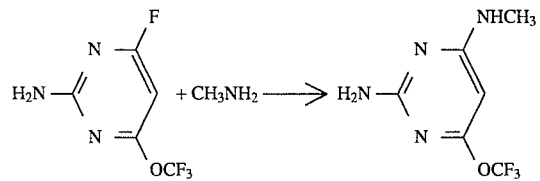

Where 2-amino-5-fluoro-6-chlorodifluoromethoxypyrimidine and sodium methylate are used, the reaction may be represented by the following equation:

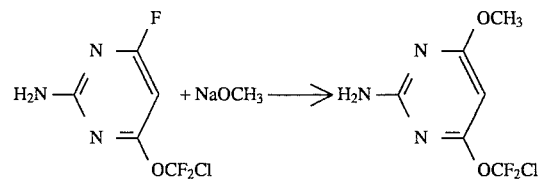

The process gives the novel 2-amino-4-fluoroalkoxypyrimidines in a high yield and purity by a simple and economical method. Contrary to expectation, fluoroalkoxy groups are not substituted. Furthermore, the chlorine atom present in the ether side chain is retained in spite of the alkaline reaction conditions. In view of the prior art (for example EP-A-70 804), all these advantageous properties are surprising.

Preferred intermediates IIIa and accordingly the preferred starting materials IIIb are those in whose formulae $R^1$ and $R^2$ are each $C_1$–$C_4$-alkyl, such as methyl, ethyl, n-propyl, isopropyl, n-butyl, sec-butyl, isobutyl or tert-butyl, $C_3$- or $C_4$-alkenyl, such as 2-propenyl, 2-methylethenyl, 2-butenyl, 3-butenyl, 1-methyl-2-propenyl or 2-methyl-2-propenyl, or $C_3$- or $C_4$-alkynyl, such as propargyl, 2-butynyl, 3-butynyl or 1-methyl-2-propynyl, and $R^1$ may furthermore be hydrogen, X is O, S or N—$R^4$, $R^4$ is hydrogen, methyl, ethyl, n-propyl, isopropyl, n-butyl, sec-butyl, isobutyl or tert-butyl, $R^8$ is hydrogen and n is 0 or 1.

The reaction of the 2-amino-4-fluoroalkoxypyrimidine IIIb with a nucleophile XVI or a salt thereof XVIa is carried out, for example, at from −80° to 80° C. Suitable nucleophiles XVI are ammonia, aliphatic amines, alcohols and thiols.

Among the amines which can be used as nucleophiles, the following should be mentioned: ammonia, methylamine, ethylamine, n-propylamine, isopropylamine, n-butylamine, isobutylamine, sec-butylamine, tert-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine, dimethylamine, diethylamine, di-n-propylamine, di-n-butylamine, N-methylethylamine, N-ethyl-n-propylamine, N-methylallylamine and N-methylpropargylamine.

Among the alcohols which can be used as nucleophiles, the following may be mentioned: methanol, ethanol, n-propanol, isopropanol, n-butanol, isobutanol, sec-butanol, tert-butanol, 2-propenol, 2-methylethenol, 2-butenol, 3-butenol, 1-methyl-2-propenol, 2-methyl-2-propenol, propynol, 2-butynol, 3-butynol and 1-methyl-2-propynol.

Among the thiols which can be used as nucleophiles, the following should be mentioned: methanethiol, ethanethiol, n-propanethiol, isopropanethiol, n-butanethiol, isobutanethiol, sec-butanethiol, tert-butanethiol, 2-butenethiol, 2-methylethenethiol, 2-butenethiol, 3-butenethiol, 1-methyl-2-propenethiol, 2-methyl-2-propenethiol, propynethiol, 2-butynethiol, 3-butynethiol and 1-methyl-2-propynethiol.

The 4-halopyrimidines IIIb can be reacted with the amines XVI in an aprotic polar solvent at from −80° to 80° C., preferably from −30° to +20° C., either the amine XVI being used in excess or an organic auxiliary base being employed.

The following solvents are suitable for the reaction of the 4-halopyrimidine IIIb with the amine XVI: Ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

Advantageously, the solvent is used in an amount of from 100 to 2,000, preferably from 400 to 1,200, % by weight, based on the starting material IIIb.

From 1.8 to 2.5, in particular from 1.95 to 2.2, mol equivalents, based on the starting material IIIb, of the amine XVI are advantageously added in the course of from 0.5 to 2 hours to a mixture of starting material IIIb in one of the abovementioned solvents at from −80° to 80° C., preferably from −30° to 25° C., and the mixture is stirred until the reaction is complete (about 3 hours) and is then allowed to warm up to 25° C. for working up.

If only about a stoichiometric amount of the amine XVI is used, advantageously from 0.9 to 1.1 equivalents, based on the starting material IIIb, of an organic auxiliary base are added. Suitable auxiliary bases are organic bases, such as trimethylamine, triethylamine, N-ethyldiisopropylamine, triisopropylamine, N,N-dimethylaniline, N,N-dimethylcyclohexylamine, N-methylpyrrolidine, pyridine, quinoline, α,β- and γ-picoline, 2,4- and 2,6-lutidine and triethylenediamine.

If the reaction is carried out with alcohols or thiols, a reaction procedure similar to that described for amines can be adopted. Advantageously, the nucleophile is added in an amount of from 0.9 to 1.3 mol equivalents, based on the starting material IIIb, in the course of from 0.5 to 2 hours, together with one of the abovementioned auxiliary bases, to a mixture of starting material IIIb in one of the abovementioned solvents at from −30° to 20° C., and the mixture is stirred until the reaction is complete (about 3 hours) and is then allowed to warm up to 25° C. for working up.

In addition to the stated solvents, other suitable solvents are ketones, e.g. acetone and methyl ethyl ketone, dipolar aprotic solvents, e.g. acetonitrile, dimethylformamide, dimethylacetamide, dimethyl sulfoxide, N-methylpyrrolidone and 1,3-dimethylimidazolin-2-one, and aromatics, e.g. benzene, toluene and xylene, or corresponding mixtures. Where alcohols are used as nucleophiles, they may advantageously be employed directly as the solvent. Salts of alcohols or thiols are particularly preferred and make it possible to dispense with the use of an organic auxiliary base. They are prepared in a known manner using alkali metals or alkaline earth metals or metal hydrides, e.g. NaH, KH, CaH$_2$ or LiH.

The reaction can be carried out under atmospheric or superatmospheric pressure, continuously or batchwise.

For working up, the reaction mixture is extracted with water to remove the salts, and the organic phase is dried and is purified, for example by chromatography. However, the reaction products are generally sufficiently pure, so that it is necessary only to filter off the precipitated salt and to evaporate down the organic phase.

Examples of preferred intermediates of the formula IIIa are:

2-amino-4-methoxy-6-trifluoromethoxypyrimidine,
2-amino-4-chlorodifluoromethoxy-6-methoxypyrimidine,
2-amino-4-ethoxy-6-trifluoromethoxypyrimidine,
2-amino-4-chlorodifluoromethoxy-6-ethoxypyrimidine,
2-amino-4-allyloxy-6-trifluoromethoxypyrimidine,
2-amino-4-allyloxy-6-chlorodifluoromethoxypyrimidine,
2-amino-4-methylthio-6-trifluoromethoxypyrimidine,
2-amino-4-chlorodifluoromethoxy-6-methylthiopyrimidine,
2-amino-4-ethylthio-6-trifluoromethoxypyrimidine,
2-amino-4-chlorodifluoromethoxy-6-ethylthiopyrimidine,
2-amino-4-methylamino-6-trifluoromethoxypyrimidine,
2-amino-4-chlorodifluoromethoxy-6-methylaminopyrimidine,
2-amino-4-ethylamino-6-trifluoromethoxypyrimidine,
2-amino-4-chlorodifluoromethoxy-6-ethylaminopyrimidine,
2-amino-4-dimethylamino-6-trifluoromethoxypyrimidine,
2-amino-4-chlorodifluoromethoxy-6-dimethylaminopyrimidine,
4-methoxy-2-methylamino-6-trifluoromethoxypyrimidine,
4-chlorodifluoromethoxy-6-methoxy-2-methylaminopyrimidine,
4-ethoxy-2-methylamino-6-trifluoromethoxypyrimidine,
4-chlorodifluoromethoxy-6-ethoxy-2-methylaminopyrimidine,
2,4-bismethylamino-6-trifluoromethoxypyrimidine,
4-chlorodifluoromethoxy-2,6-bismethylaminopyrimidine,
4-ethylamino-2-methylamino-6-trifluoromethoxypyrimidine,
4-chlorodifluoromethoxy-6-ethylamino-2-methylaminopyrimidine,
4-dimethylamino-2-methylamino-6-trifluoromethoxypyrimidine,
4-chlorodifluoromethoxy-6-dimethylamino-2-methylaminopyrimidine.

Embodiment C:

A sulfonamide of the formula V is reacted in a conventional manner (EP-A-141 777) with about the stoichiometric amount of phenyl carbamate VI in an inert organic solvent at from 0° to 120° C., preferably from 20° to 100° C. The reaction can be carried out at atmospheric or superatmospheric pressure (up to 50, preferably from 1 to 5, bar), continuously or batchwise.

Suitable solvents in addition to those stated in the literature cited above are, for example, nitrohydrocarbons, such as nitroethane and nitrobenzene, nitriles, such as acetonitrile and benzonitrile, esters, such as ethyl acetate, amides, such as dimethylformamide, and/or ketones, such as acetone. The reaction is preferably carried out in ethyl acetate as the solvent and using pyridine or one of the abovementioned tertiary amines as the base.

The sulfonamides of the formula V may be obtained by reacting the corresponding sulfonyl chlorides with ammonia (M. Quaedvlieg in Houben-Weyl, Methoden der organischen Chemie, Georg Thieme Verlag, Stuttgart, Vol. 9 (1955), 398–400, F. Muth, ibid. 605 et seq.). However, it is also possible, in a nucleophilic substitution, to react an o-halobenzenesulfonamide, for example, with an alcohol or thiol and, for example, to oxidize the resulting thioether to the sulfoxide or sulfone (cf. process examples).

The corresponding sulfonyl chlorides for the preparation of the sulfonamides of the formula V are obtained in general by a Meerwein reaction (diazotization of suitable amines and sulfochlorination with sulfur dioxide under catalysis with a copper salt: F. Muth in Houben-Weyl, Methoden der organischen Chemie, Georg Thieme Verlag, Stuttgart, Vol. 9 (1955), 579, S. Pawlenko in Houben-Weyl, Methoden der organischen Chemie, Georg Thieme Verlag, Stuttgart, Vol. E 11/2 (1985), 1069), from the corresponding sulfonic acids (F. Muth in Houben-Weyl, Methoden der organischen Chemie, Georg Thieme Verlag, Stuttgart, Vol. 9 (1955), 564), by chlorosulfonation of suitable aromatic intermediates (F. Muth, ibid., page 572) or by oxidative chlorination of sulfur intermediates having a low functionality (mercaptans, diaryl disulfides, S-benzylmercaptans) (F. Muth, ibid. page 580, S. Pawlenko, loc. cit., page 1073). Ortho-cyano-substituted benzenesulfonyl chloride can often advantageously be obtained by ring cleavage of corresponding saccharins with phosphorus pentachloride (J. Chem. Soc. 89 (1906), 352).

The sulfonyl isocyanates of the formula II which are required as starting materials can be obtained in a conventional manner from the corresponding sulfonamides by phosgenation (Houben-Weyl 11/2 (1985), 1106 and U.S. Pat. No. 4,379,769) or by reacting the sulfonamides with chlorosulfonyl isocyanate (German Laid-Open Application DOS 3,132,944).

The sulfonylcarbamates of the formula IV were prepared by, or similarly to, known reactions (for example EP-A 120 814). However, the sulfonyl isocyanates of the formula I can also be converted into the carbamates of the formula IV with phenol in a smooth reaction in an inert solvent, such as ether or dichloromethane.

Carbamates of the formula IV are obtainable by known reactions (for example EP-A 101 670) or by reactions similar to these, but can also be prepared from corresponding isocyanates by reaction with phenol.

The isocyanates are obtained from the amides of the formula III by treatment with oxalyl choride or phosgene (similarly to Angew. Chem. 83 (1971), 407 and EP-A 388 873).

Sulfonylureas of the formula I which have the meanings specified under claim 8 can also be prepared by reacting sulfonation or acylation reagents VIb,d with 2-amino-, 2-alkylamino- or 2-hydroxybenzenesulfonylureas VIa or VIc.

2-Aminobenzenesulfonylureas of the formula VIa are obtained by catalytic hydrogenation of the correspondingly substituted 2-nitrobenzenesulfonylureas in an inert organic solvent, for example methanol, ethanol, dioxane or ethyl acetate, it being possible to use metal or metal oxides on carriers, such as Pd/active carbon, Raney nickel or $PrO_2$, as catalysts (group of authors in Organikum, VEB Deutscher Verlag der Wissenschaften, Berlin (1955), 645–649).

2-Alkylaminobenzenesulfonylureas of the formula VIa are prepared from the correspondingly substituted 2-aminobenzenesulfonylurea by alkylation with suitable alkyl halides, dialkyl sulfates or alkyl tosylates.

2-Hydroxybenzenesulfonylureas of the formula VIc are prepared, for example, by catalytic hydrogenation of suitably substituted 2-benzyloxybenzenesulfonylureas, the abovementioned solvents and catalysts being used.

A sulfonylurea of the formula IVa,c is reacted in a conventional manner (J. March in "Advanced Organic Chemistry", J. Wiley & Sons, New York (1985), pages 370–371 and 346–351 and the literature cited there), in an inert organic solvent, with about the stoichiometric amount of the acylation or sulfonation reagent VIb,d, in the presence of an auxiliary base VIe at from 0° to 120° C., preferably from 0° to 100° C. The reaction can be carried out under atmospheric or superatmospheric pressure (up to 50 bar), preferably at 1 bar, continuously or batchwise. Suitable solvents are stated in the abovementioned literature, examples being acetonitrile, tetrahydrofuran, ethylacetate, dimethylformamide, N-methyl-2-pyrrolidone or acetone. Suitable auxiliary bases VIe are the tertiary amines mentioned for process variant B or alkali metal carbonates. The reaction is preferably carried out in acetonitrile, tetrahydrofuran or dimethylformamide, in the presence of pyridine or potassium carbonate.

Because of the biological activity, preferred compounds of the formula I or salts thereof are those in which the substituents have the following meanings:

$R^1$ is hydrogen or methyl, $R^2$ is fluorine, chlorine, bromine or trifluoromethyl (m=0), or methyl, ethyl, n-propyl or isopropyl (m=1), $R^3$ is hydrogen, fluorine, chlorine, bromine, methyl, methoxy, trifluoromethyl or trifluoromethoxy, X is oxygen, sulfur or an amino group —$NR^4$, $R^4$ is hydrogen, methyl or ethyl, A is $NO_2$, $NH_2$, OH, CN, SCN, an ether group, such as $OCH_3$ or $OC_2H_5$, it being possible for the methyl group furthermore to carry 1 to 3 halogen atoms and the ethyl group 1 to 4 halogen atoms, in particular fluorine or chlorine, or for both radicals to carry a methoxy group, or A is sulfide, sulfoxyde, sulfonyl, sulfonamido, e.g. $SO_2$—N-di-$C_1$-$C_4$-alkylamino, carbonate, acyloxy or acyl, e.g. acetoxy or acetyl, $R^5$ is $C_1$-$C_3$-alkyl, such as methyl, ethyl, n-propyl or isopropyl, alkenyl, such as allyl, crotyl or but-1-en-3-yl, alkynyl, such as propargyl, but-1-yn-3-yl or but-2-ynyl, haloalkyl, such as 2-chloroethyl, 2-chloro-n-propyl, 3-chloro-n-propyl, 1-chlorobut-2-yl, 2-chloroisobutyl, 4-chloro-n-butyl, chloro-tert-butyl, 3-chloroprop-2-yl, 2,2,2-trifluoroethyl or trifluoromethyl, alkoxyalkyl, such as 2-methoxyethyl, 3-ethoxyethyl, 3-methoxy-n-propyl, 2-methyl-n-propyl, 3-methoxy-n-butyl, 1-methoxybut-2-yl, methoxy-tert-butyl, 2-methoxy-n-butyl or 4-methoxy-n-butyl, alkoxyalkoxyalkyl, such as 2-methoxyethoxymethyl, 2-(ethoxy)-ethoxymethyl, 2-(propoxy)-ethoxymethyl, 2-methoxyethoxyethyl, 2-(ethoxy)-ethoxyethyl or 2-(methoxymethoxy)-ethyl, haloalkoxyalkyl, such as 2-(β-chloroethoxy)-ethyl, 3-(β-chloroethoxy)-n-propyl or 3-(γ-chloro-n-propoxy)-n-propyl, or cycloalkyl, such as cyclopropyl, cyclopentyl or cyclohexyl, $R^6$ is hydrogen, alkoxy, such as methoxy or ethoxy, or alkyl, such as methyl, ethyl, n-propyl, isopropyl or n-butyl, or, together with $R^7$, is tetramethylene, pentamethylene, hexamethylene, ethyleneoxyethylene or ethylene-N-methyliminoethylene, $R^7$ is alkyl, such as methyl, ethyl, n-propyl or isopropyl, haloalkyl as stated above for $R^5$, difluoromethyl, trifluoromethyl, chlorodifluoromethyl, 1,1,2,2-tetrafluoroethyl, 2,2,2-trifluoroethyl or 2-chloro-1,1,2-trifluoroethyl, alkoxyalkyl as stated above for $R^5$, or cycloalkyl, such as cyclopropyl, cyclobutyl or cyclopentyl, $R^8$ is hydrogen or halogen, such as fluorine or chlorine, preferably hydrogen, and m, n, o, p and q are each 0 or 1, and o is additionally 2, and, where p=0, q is likewise 0.

Sulfonylureas of the formula I in which $R^1$ is hydrogen or methyl;

$R^2$ is halogen or trifluoromethyl when m is 0 and is methyl when m is 1;

X is O or NH;

$R^3$ is hydrogen, halogen, methyl or methoxy;

A is $NO_2$, $N[CH_3]SO_2CH_3$, a group $SO_2R^5$, where $R^5$ is $C_1$–$C_4$-alkyl, a group $SO_2NR^6R^7$, where $R^6$ and $R^7$ are each methyl, or an $OR^7$ group, where $R^7$ is $C_1$–$C_2$-alkyl which may carry from 1 to 3 or 4 halogen atoms or a methoxy group, and $R^8$ is hydrogen, and environmentally compatible salts thereof are particularly preferred.

The salts of the compounds I are obtainable in a conventional manner (EP-A-304 282, U.S. Pat. No. 4,599,412). They are obtained by deprotonating the corresponding sulfonylureas I in water or in an inert organic solvent at from −80° to 120° C., preferably from 0° to 60° C., in the presence of a base.

Examples of suitable bases are alkali metal and alkaline earth metal hydroxides, hydrides, oxides or alcoholates, such as sodium, potassium and lithium hydroxide, sodium methylate, ethylate and tert-butylate, sodium and calcium hydride and calcium oxide. Salts having other counter-ions, such as ammonium, tetraalkylammonium, benzyltrialkylammonium, phosphonium, sulfonium and the like, can be prepared therefrom by cation exchange.

Examples of suitable solvents in addition to water are alcohols, such as methanol, ethanol and tert-butanol, ethers, such as tetrahydrofuran and dioxane, acetonitrile, dimethylformamide, ketones, such as acetone and methyl ethyl ketone, and halogenated hydrocarbons.

The deprotonation can be carried out at atmospheric pressure or at up to 50 bar, preferably at from atmospheric pressure to 5 bar gauge pressure.

Suitable salts of the compounds of the formula I are agriculturally useful salts, for example alkali metal salts, such as the potassium or sodium salt, alkaline earth metal salts, such as the calcium, magnesium or barium salt, manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

The novel herbicidal and growth-regulating compounds I or the agents containing them can be used, for example, in the form of directly sprayable solutions, powders, suspensions, including concentrated aqueous, oily or other suspensions or dispersions, emulsions, oil dispersions, pastes, dusts, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives are mineral oil fractions having medium to high boiling points, such as kerosene or diesel oil, as well as coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substances, as such, can be dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil, and which are suitable for dilution with water.

Suitable surfactants are the alkali metal, alkaline earth metal and ammonium salts of aromatic sulfonic acids, for example, lignin-, phenol-, naphthalene- and dibutylnaphthalenesulfonic acid, and of fatty acids, alkylsulfonates and alkylarylsulfonates, alkylsulfonates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ether, tributylphenyl polyglycol ether, alkylaryl polyether alcohols, isotridecyl alcohol, fatty alcohols/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents and dusts can be prepared by mixing or milling the active ingredients together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate, ureas and vegetable products, such as grain flours, bark meal, wood meal and nutshell meal, cellulosic powders or other solid carriers.

The formulations contain from 0.1 to 95, preferably from 0.5 to 90, % by weight of active ingredients. The active ingredients are used in a purity of from 90 to 100%, preferably from 95 to 100% (according to the NMR spectrum).

The novel compounds I can be formulated, for example, as follows:

I. 90 parts by weight of compound No. 1.003 are mixed with 10 parts by weight of N-methyl-α-pyrrolidone, and a solution which is suitable for use in the form of very small drops is obtained.

II. 20 parts by weight of compound No. 1.005 are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 2.005 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 5.001 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 5.003 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 6.001 are mixed with 97 parts by weight of finely divided kaolin. A dust which contains 3% by weight of the active ingredient is obtained in this manner.

VII. 30 parts by weight of active ingredient No. 9.001 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 9.011 are thoroughly mixed with 2 parts by weight of the calcium salt of dodecylbenzenesulfonic acid, 8 parts by weight of the fatty alcohol polyglycol ether, 2 parts by weight of the sodium salt of a phenol/urea/formaldehyde condensate and 68 parts by weight of a paraffinic mineral oil. A stable oily dispersion is obtained.

The application of the herbicidal and growth-regulating agents or of the active ingredients can be effected by the pre-emergence or post-emergence method. If the active ingredients are less well tolerated by certain crops, it is possible to use application methods in which the herbicides are sprayed with the aid of sprayers in such a way that the leaves of the sensitive crops are as far as possible not affected, while the active ingredients reach the leaves of undesirable plants growing underneath or the uncovered soil surface (post-directed, lay-by).

The application rates of active ingredient when used as herbicides is from 0.001 to 5, preferably from 0.01 to 2, kg/ha of active ingredient (a.i.), depending on the aim of control, the season, the target plants and the stage of growth.

Some of the large number of various potential applications of the novel compounds of the formula I as plant growth regulators in plant cultivation, in agriculture and in horticulture, are mentioned below.

A. The compounds which can be used according to the invention can be employed for greatly inhibiting the vegetative growth of the plants, which manifests itself in particular in a reduction in the growth in length. Accordingly, the treated plants have a stunted growth; a darker leaf color is also observed.

The increase in the stability of crops susceptible to lodging, such as cereals, corn, sunflowers and soybean, is also of economic interest. The resulting shortening and strengthening of the stems reduce or eliminate the danger of lodging of plants under unfavorable weather conditions prior to the harvest.

B. The growth regulators make it possible to achieve higher yields of both plant parts and plant ingredients. For example, it is possible to induce the growth of larger amounts of buds, blossoms, leaves, fruits, seeds, roots and tubers, to increase the content of sugar in sugar beet, sugar cane and citrus fruits, to increase the protein content of cereals or soybean or to stimulate rubber trees to produce more latex.

C. Finally, plant growth regulators can be used both to shorten or lengthen the stages of development and to achieve an acceleration or retardation in the ripening of the harvested plant parts before or after the harvest.

Furthermore, growth regulators can be used to reduce the water consumption of plants. This is particularly important for agricultural areas which have to be artificially irrigated at high expense, for example in arid or semi-arid regions. By using the novel substances, it is possible to reduce the intensity of irrigation and hence to carry out more economical farming.

The growth regulators of the formula I can be fed to the crops both through the seed (as a seed dressing) and via the soil, ie. through the root and, particularly preferably, via the foliage by spraying.

In view of the versatility of the application methods, the novel compounds or agents containing them can be used in a large number of crops, eliminating undesirable plants.

| List of crops: | |
|---|---|
| Botanical name | Common name |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugar beets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | beets |
| *Camellia sinesis* | tea plants |
| *Carthamus tinctorius* | safflower |
| *Carya illinoinensis* | pecan trees |
| *Citrus limon* | lemons |
| *Citrus sinesis* | orange trees |
| *Coffea arabica* (*Coffea canephora*, *Coffea liberica*) | coffee plants |
| *Cucumis sativus* | cucumbers |
| *Cynodon dactylon* | Bermudagrass |
| *Daucus carota* | carrots |
| *Elaeis guineensis* | oil palms |
| *Fragaria vesca* | strawberries |
| *Glycine max* | soybeans |
| *Gossypium hirsutum* | cotton |

19
-continued

List of crops:

| Botanical name | Common name |
|---|---|
| (Gossypium arboreum | |
| Gossypium herbaceum | |
| Gossypium vitifolium) | |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linium usitatissimum | flax |
| Lycopersicon lycopersicum | tomatoes |
| Malus spp. | |
| Manihot esculenta | cassava |
| Medicago sativa | alfalfa (lucerne) |
| Musa spp. | banana plants |
| Nicotiana tabacum | tobacco |
| (N. rustica) | |
| Olea europaea | olive trees |
| Oryza sativa | rice |
| Phaseolus lunatus | limabeans |
| Phaseolus vulgaris | snapbeans, green beans. dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cocoa plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweetcorn, maize |

In order to broaden the action spectrum and to achieve synergistic effects, the novel compounds I can be mixed with a large number of members of other groups of herbicidal or growth-regulating active ingredients and applied together with them. For example, diazine, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, and aryloxy- and hetaryloxyphenoxypropionic acids and their salts, esters and amides and others are suitable components for the mixture.

In addition, it may be useful to apply the compounds I, alone or in combination with other herbicides, also as a mixture together with further crop protection agents, for example with pesticides or agents for controlling phytopathogenic fungi or bacteria. The miscibility with mineral salt solutions which are used for the treatment of nutrient and trace element deficiencies is also of interest. Non-phytotoxic oils and oil concentrates may also be added.

SYNTHESIS EXAMPLES

The methods stated in the examples below were used for obtaining further compounds of the formula I with appropriate modification of the starting compounds; the compounds obtained are shown in the tables below with physical data; compounds without these data can be synthesized in a similar manner from the corresponding substances. Owing to their close structural relationship with the prepared and investigated compounds, they are likely to have a similar action.

I. Preparation of the intermediates

Example I.1

2-Chloro-4-trichloromethoxy-6-trichloromethylpyrimidine a) 2-Chloro-4-methoxy-6-trichloromethylpyrimidine 293.1 g (1.692 mol) of 30% strength sodium methylate solution were added to a solution of 434 g (1.692 mol) of 2,6-dichloro-4-trichloromethylpyrimidine in 1 l of 1,2-dichloroethane in the course of 1½ hours at from 0° to 5° C. while stirring. Stirring was continued for 1 hour at from 0° to 5° C. and for 12 hours at 25° C. The reaction mixture was extracted with water and with saturated sodium chloride solution. Drying over magnesium sulfate and evaporating down gave 423 g (95% of theory) of the title compound as a virtually colorless oil of $n_D^{23}=1.5552$. $^1$H-NMR (CDCl$_3$) (ppm OCH$_3$ (s/3H) 4.1; CH (s/1H) 7.25.

b) 2-Chloro-4-trichloromethoxy-6-trichloromethylpyrimidine

Chlorine was passed, initially at 110° C., into a mixture of 210 g (0.802 mol) of a) and 260 mg (0.0016 mol) of α,α'-azoisobutyronitrile with exposure to UV light and gas chromatographic monitoring of the course of the reaction, a reaction temperature of 140° C. being established even after removal of the heating bath. After the reaction had died down, a total of 341 g (4.8 mol) of chlorine were passed in for 5½ hours at 120° C. From 40° C., 70 ml of n-pentane were stirred into the cooling reaction mixture for precipitation. The precipitate was filtered off under suction, washed with petroleum ether and dried, 163 g (55% of theory) of the title compound of melting point 67°–69° C. being obtained.

According to the gas chromatogram, the filtrate (113.8 g) consisted of 83% of the title compound, 4% of 2-chloro-4-dichloromethoxy-6-trichloromethylpyrimidine and 9% of 2,4-dichloro-6-trichloromethylpyrimidine. The total yield of the title compound was 87.6% of theory.

Example I.2

2,4-Difluoro-6-trichloromethoxypyrimidine a) 2,4-Difluoro-6-methoxypyrimidine (Preparation according to the process of the prior German Patent Application P 39 00 471 (O.Z. 0050/40474)

335.8 g (1.865 mol) of 30% strength sodium methylate (in methanol) were added to a mixture of 250 g (1,865 mol) of 2,4,6-trifluoropyrimidine in 1.4 l of methanol at −20° C. in the course of 45 minutes and stirring was continued for a further 30 minutes at this temperature. Thereafter, the reaction mixture was allowed to warm up to 25° C. and was evaporated down to about ⅕th of its volume.

The mixture thus obtained was partitioned between diethyl ether and water, after which the organic phase was dried over magnesium sulfate and evaporated down. After distillation (1.1 m column, 3 mm V packings), 141.6 g (52% of theory) of the title compound of boiling point 144°–145° C. were obtained.

114.4 g (42% of theory) of 4,6-difluoro-2-methoxypyrimidine of boiling point 157°–161° C. were obtained from the distillation residue by distillation over a Normag attachment.

b) 2,4-Difluoro-6-trichloromethoxypyrimidine 210 g (2.96 mol) of chlorine were passed into 123 g. (0.843 mol) of 2,4-difluoro-6-methoxypyrimidine in the course of 2½ hours while stirring at 130° C., with exposure to UV light and gas chromatographic monitoring of the course of the reaction. The reaction mixture was distilled under reduced pressure over a 10 cm Vigreux column, 190.2 g (90.5% of theory) of the title compound of boiling point 40°–43° C./0.2 mbar being obtained.

Example I.3

2,4-Dichloro-6-trichloromethoxypyrimidine 303 g (4.27 mol) of chlorine were passed into a mixture of 209 g (1.168 mol) of 2,6-dichloro-4-methoxypyrimidine and 2 g (0.012 mol) of α,α'-azoisobutyronitrile in the course of half an hour at 80° C., 1 hour at 100° C., 3 hours at 120° C. and 3 hours at 150° C., with stirring, exposure to UV light and gas chromatographic monitoring of the course of the reaction. Thereafter, the reaction mixture was distilled under reduced pressure over a 50 cm column containing 4 mm V2-A Raschig rings. 41.3 g (73% of theory) of the title compound of boiling point 87°–88° C./0.4 mbar and melting point 55°–56° C. were obtained.

Example I.4

2,4-Difluoro-6-trifluoromethoxypyrimidine 49.9 g (0.2 mol) of 2,4-difluoro-6-trichloromethoxypyrimidine were added to a mixture of 39.3 g (0.22 mol) of antimony trifluoride and 9.38 g (0.031 mol) of antimony pentachloride at 100° C. in the course of 15 minutes while stirring.

The bath temperature was increased from 100 to 150° C. in the course of 25 minutes and stirring was continued for 30 minutes, reflux being established at from 120° to 125° C. 37.1 g (92.7% of theory) of the title compound of boiling point 125°–127° C. and $n_D^{23}$=1.3787 were obtained by subsequent distillation.

Example I.5

6-Chlorodifluoromethoxy-2,4-difluoropyrimidine 93 g (0.373 mol) of 2,4-difluoro-6-trichloromethoxypyrimidine were added to a mixture of 44.5 g (0.249 mol) of antimony trifluoride and 0.94 g (0.0031 mol) of antimony pentachloride at 100° C. in the course of 10 minutes while stirring. The bath temperature was increased from 100° to 175° C. in the course of 25 minutes, reflux being established at 145° C. Stirring was carried out for 1½ hours, after which the reaction product was distilled off at 146°–150° C. The distillate was dissolved in 200 ml of methylene chloride, extracted twice with 6N hydrochloric acid and dried over magnesium sulfate. Evaporating down under reduced pressure gave, as the residue the title compound of $n_D^{23}$=1.4142 in a yield of 63.7 g (78.8% of theory).

Example I.6

2-Fluoro-4-trifluoromethoxy-6-trifluoromethylpyrimidine 80 g (0.219 mol) of 2-chloro-4-trichloromethyl-6-trichloromethoxypyrimidine were added to a mixture of 93.9 g (0.525 mol) of antimony trifluoride and 18.7 g (0.0627 mol) of antimony pentachloride in the course of 5 minutes while stirring at 100° C. The bath temperature was increased to 140° C. in the course of 10 minutes and stirring was continued for 1 hour, a strong reflux being established. The reaction product was distilled over at 135°–140° C., and at 95° C./50 mbar toward the end. The distillate was taken up in methylene chloride, the solution was extracted with 6N hydrochloric acid and the organic phase was dried over magnesium sulfate. Evaporating down under reduced pressure gave the title compound in a yield of 35.9 g (65.5% of theory).

Example I.7

2,4-Dichloro-6-trifluoromethoxypyrimidine 115 g (0.407 mol) of 2,4-dichloro-6-trichloromethoxypyrimidine were added to a mixture of 80 g (0.447 mol) of antimony trifluoride and 18.77 g (0.0627 mol) of antimony pentachloride in the course of 5 minutes while stirring at 100° C., the reaction temperature increasing to 140° C. Stirring was continued for a further 45 minutes at 150° C. A pressure of 210 mbar was established for distillation, the title compound passing over at 128° C.; final volatile components were distilled off at 110° C./22 mbar. The distillate was dissolved in methylene chloride, the solution was extracted 3 times with 6N hydrochloric acid and the organic phase was dried over magnesium sulfate. Evaporating down under reduced pressure gave the title compound in a yield of 80 g (84 4% of theory), as a colorless oil of $n_D^{25}$=1.4604.

Example I.8

2-Amino-4-chlorodifluoromethoxy-6-fluoropyrimidine 9.8 g (0.578 mol) of gaseous ammonia were passed into a mixture of 62.5 g (0.289 mol) of 2,4-difluoro-6-chlorodifluoromethoxypyrimidine in 300 ml of tetrahydrofuran in the course of one hour at from −75° to −70° C. while stirring. Stirring was continued for one hour at −70° C., after which the mixture was heated to room temperature. The precipitate which separated out was filtered off under suction and partitioned between ethyl acetate and water, and the organic phase was dried over magnesium sulfate. The reaction filtrate was evaporated down, the residue was dissolved in the above ethyl acetate phase and the solution was chromatographed over silica gel using 5:1 petroleum ether/ether and was evaporated down. 46.5 g (75.3% of theory) of the title compound were obtained as colorless crystals of melting point 77°–80° C.

Example I.9

2-Amino-4-floro-6-trifluoromethoxypyrimidine 8.7 g (0.51 mol) of gaseous ammonia were passed into a mixture of 51 g (0.255 mol) of 2,4-difluoro-6-trifluoromethoxypyrimidine in 200 ml of diethyl ether in the course of 1 hour at from −75° to −70° C. while stirring. Stirring was continued for a further 1½ hours at −70° C. and for 1 hour at room temperature. The reaction mixture was evaporated down under reduced pressure, the residue was taken up in methylene chloride and the solution was extracted with water. After the organic phase had been dried, evaporated down and chromatographed over silica gel using 8:1 petroleum ether/ether, 38.1 g (75.6% of theory) of the title compound were obtained as colorless crystals of melting point 86°–89° C.

Example I.10

2-Amino-4-chloro-6-trifluoromethoxypyrimidine 4.3 g (0.25 mol) of gaseous ammonia were passed into a mixture of 23.3 g (0.1 mol) of 2,4-dichloro-6-trifluoromethoxypyrimidine in 150 ml of methyl tert-butyl ether in the course of 45 minutes while stirring at −50° to −45° C. Stirring was continued for 30 minutes at −50° C., for 1 hour at −30° C. and for 1 hour at 25° C. The precipitate which separated out was filtered off under suction, washed with water and dried, 5.4 g (33.1% of theory) of 4-amino-2,4-dichloropyrimidine of melting point 270°–272° C. being obtained as a byproduct. The filtrate was washed with water, dried, partially evaporated down under reduced pressure and subjected to fractional chromatography using 5:1 petroleum ether/ether, 3 g (12.8% of theory) of starting material being obtained as a colorless oil from the first fractions and 9 g (42% of theory) of the title compound being obtained as colorless crystals of melting point 55°–56° C. from the final fraction. The conversion was 48.3%.

Example I.11

4-Chlorodifluoromethoxy-6-fluoro-2-methylaminopyrimidine 20.3 g (0.0938 mol) of 4-chlorodifluoromethoxy-2,6-difluoropyrimidine in 150 ml of tetrahydrofuran were initially taken, and 5.8 g (0.188 mol) of gaseous methylamine were added at from −70° to −60° C. in the course of 30 minutes while stirring. Stirring was continued for 1 hour in each case at −70° C., 0° C. and 25° C. The reaction mixture was evaporated down under reduced pressure, after which the residue was stirred with water, the solution was extracted twice with ethyl acetate and the extract was dried over magnesium sulfate. It was partially evaporated down under reduced pressure and then subjected to fractional chromatography over silica gel using 1:5 ether/petroleum ether. The first fractions contained the title compound of melting point 57°–61° C. in a yield of 12.5 g (58.5%).

Example I.12

2-Amino-4-trifluoromethoxy-6-trifluoromethylpyrimidine 4.7 g (0.278 mol) of gaseous ammonia were passed into a mixture of 38.0 g (0.147 mol) of 2-fluoro(chloro)-4-trifluoromethoxy-6-trifluoromethylpyrimidine in 150 ml of diethyl ether while stirring at from −75° to −70° C. in the course of 1 hour. Stirring was continued for 2 hours in each case at −75° C. and, after heating, at 25° C. The precipitate which separated out was filtered off under suction, after which the organic phase was extracted with water, dried and partially evaporated down. Chromatography over silica gel using methyl tert-butyl ether gave 20.4 g (56.1% of theory) of the title compound of melting point 47°–49° C.

II. Preparation of the intermediates IIIa

Example II.1

2-Amino-4-methoxy-6-trifluoromethoxypyrimidine 2.7 g (0.015 mol) of 30% strength sodium methylate were added to 2.95 g (0.015 mol) of 2-amino-4-fluoro-6-trifluoromethoxypyrimidine in 50 ml of methanol in the course of 15 minutes while stirring at from −5° to 0° C. After stirring for 1 hour at 0° C. and heating to 25° C., the reaction mixture was evaporated down under reduced pressure, stirred with water and extracted with methylene chloride. Drying and evaporating down under reduced pressure gave 3.1 g (98% of theory) of the title compound of $n_D^{25}$=1.4770.

Example II.2

2-Amino-4-chlorodifluoromethoxy-6-methoxypyrimidine 26.1 g (0.145 mol) of 30% strength sodium methylate were added to 31.0 g (0.145 mol) of 2-amino-4-chlorodifluoromethoxy-6-fluoropyrimidine in 300 ml of methanol in the course of 15 minutes while stirring at from −10° to 0° C. Stirring was continued for 30 minutes at 0° C. and for 1 hour at 25° C. The reaction mixture was evaporated down under reduced pressure and worked up as above. 31.6 g (96.6% of theory) of the title compound were obtained as a colorless oil of $n_D^2$=1.5039.

Example II.3

4-Chlorodifluoromethoxy-2-methylamino-6-methoxypyrimidine 4.7 g (0.026 mol) of 30% strength sodium methylate were added to 6.0 g (0.0263 mol) of 4-chlorodifluoromethoxy-6-fluoro-2-methylaminopyrimidine in 100 ml of methanol in the course of 10 minutes while stirring at 0° C. Stirring was continued for 1 hour at 0° C. and for 1 hour at 25° C. Conventional working up gave 6.3 g (100% of theory) of the title compound of melting point 49°–53° C.

Example II.4

4-Chlorodifluoromethoxy-6-dimethylamino-2-methylaminopyrimidine 1.9 g (0.0417 mol) of gaseous dimethylamine were passed into a mixture of 8.9 g (0.0417 mol) of 2-amino-4-chlorodifluoromethoxy-6-fluoropyrimidine in 100 ml of tetrahydrofuran in the course of 10 minutes while stirring at 0° C. Stirring was continued for 1 hour at 0° C. and for 2 hours at 25° C. Conventional working up gave 9.7 g (97.5% of theory) of the title compound of melting point 127°–130° C.

III. Preparation of the intermediates II 2-(Ethylsulfonyl)benzenesulfonyl isocyanate a) 2-(Ethylthio)benzenesulfonamide 62 g (1.0 mol) of ethanethiol were added to a mixture of 65.9 g (1.0 mol) of 85% strength potassium hydroxide powder and 500 ml of dimethylformamide at 25° C. while stirring, and stirring was continued for 15 minutes. Thereafter, a solution of 95.8 g (0.5 mol) of 2-chlorobenzenesulfonamide was added at 90° C. while stirring in the course of 30 minutes, and stirring was continued for 8 hours at 110° C. The mixture was cooled and was evaporated down under reduced pressure, after which the residue was partitioned between methylene chloride and water, and the organic phase was washed with dilute sodium chloride solution. Evaporating down under reduced pressure gave 88.4 g (81.5% of theory) of the title compound as a semicrystalline mass.

b) 2-(Ethylsulfonyl)benzenesulfonamide 81.6 g (1.2 mol) of 50% strength hydrogen peroxide were added to a mixture of 88 g (about 0.4 mol) of crude 2-(ethylthio)benzenesulfonamide in 200 ml of glacial acetic acid in the course of 30 minutes while stirring at 60° C., and stirring was continued overnight at 25° C. After stirring had been carried out for a further 4 hours at 60° C., the mixture was cooled and poured onto 500 ml of ice water. The precipitate which had separated out was filtered off under suction, washed with water and dried under reduced pressure at 50° C., 72.3 g (72.5% of theory) of the title compound of melting point 179°–181° C. being obtained.

c) 2-(Ethylsulfonyl)benzenesulfonyl isocyanate 102.8 g (0.865 mol) of thionyl chloride were added to 71.8 g (0.288 mol) of 2-(ethylsulfonyl)benzenesulfonamide in 500 ml of 1,2-dichloroethane in the course of 30 minutes while stirring at from 70° to 80° C., and the refluxed mixture was stirred for 2.5 hours. After the mixture had been cooled to 50° C., 2 ml of pyridine were added and gaseous phosgene was passed into the refluxed mixture in the course of 5 hours while stirring. Evaporating down gave 84.1 g of the title compound, which was taken up directly in 1,2-dichloroethane for storage.

2-(Methylsulfinyl)benzenesulfonyl isocyanate a) 2-(Methylsulfynyl)benzenesulfonamide 14.8 g of of hydrogen peroxide (30% strength in $H_2O$) (0.13 mol) were added dropwise at from 25° to 30° C. to a suspension of 26.5 g (0.13 mol) of 2-(methylthio)benzenesulfonamide (prepared similarly to 2-(ethylthio)benzenesulfonamide) and 2.1 g of $Na_2WO_4 \cdot 2H_2O$ in 88 ml of glacial acetic acid. The suspension clarified to give a homogeneous solution, from which a precipitate rapidly separated out. Stirring was carried out for 45 minutes at 25° C., the batch was poured onto 400 ml of $H_2O$ and the precipitate was filtered off under suction. It was washed with water and dried at 40° C. under reduced pressure from a water pump. 24.3 g (85% of theory) of the title compound were obtained in this manner.

$^1$H NMR spectrum (250 MHz, $CD_3SOCD_3$, int. TMS): 8.16 d (1H), 7.82–8.0 m (2H), 7.77 br (2H), 7.63–7.85 m (2H), 2.76 s (3H).

b) N-(n-Butylamino)carbonyl-2-methylsulfynylbenzenesulfonamide 10.2 g (0.10 mol) of n-butyl isocyanate were added dropwise at 25° C. to a suspension of 20.1 g (0.09 mol) of 2-(methylsulfynyl)benzenesulfonamide in 250 ml of acetonitrile. After the addition of 13.9 g (0.10 mol) of potassium carbonate, the refluxed mixture was stirred for 4 hours. The mixture was cooled to 0° C. and then poured onto 400 ml of ice/water, the pH was brought to 1 by adding concentrated hydrochloric acid and the solution was extracted with twice 250 ml of methylene chloride. The organic extracts were washed neutral with water and dried over $Na_2SO_4$. After removal of the solvent, 25.0 g of the title compound (85% of theory) were obtained as a pale brown oil.

$^1$H NMR spectrum (250 MHz, $CDCl_3$, int. TMS): 8.28 d (1H), 7.89 t (1H), 7.73 t (1H), 6.03 t (1H), 3.13 m (2H), 2.95 s (3H), 1.38 m (2H), 1.24 m (2H), 0.85 t (3H).

c) 2-(Methylsulfynyl)benzenesulfonyl isocyanate

Phosgene was passed slowly into a solution of 25.0 g of N-(n-butylamino)carbonyl-2-methylsulfynylbenzenesulfonamide and 0.4 g of 1,4-diazabicyclo[2.2.2]octane in 400 ml of xylene under reflux (cooling with solid carbon dioxide) until an internal temperature of 100° C. was reached. The cooling was removed and the volatile components were distilled off at 80° C. under reduced pressure from a water pump. The remaining sulfonyl isocyanate was reacted without further purification.

2-[N,N-(Dimethylamino)sulfonyl]benzenesulfonyl isocyanate a) N-(n-Butylamino)carbonyl-2-(N,N-dimethylaminosulfonyl)benzenesulfonamide 18.6 g (0.18 mol) of n-butyl isocyanate were added dropwise at 25° C. to a suspension of 44.2 g (0.17 mol) of 2-[(N,N-dimethylamino)sulfonyl]benzenesulfonamide (prepared similarly to 2-[(N,N-diethylamino)sulfonyl]benzenesulfonamide in U.S. Pat. No. 4,310,346) in 450 ml of acetonitrile. After the addition of 25.4 g (0.18 mol) of potassium carbonate, the refluxed mixture was stirred for 3 hours. It was cooled to 0° C., after which 400 ml of ice/water were added, the pH was brought to 1 by adding concentrated hydrochloric acid and the precipitate formed was filtered off under suction, washed neutral with water and dried at 40° C. under reduced pressure from a water pump. 60.0 g of the title compound (99% of theory) were obtained in this manner as a pale yellow powder.

$^1$H NMR spectrum (250 MHz, $CDCl_3$, int. TMS): 8.55 br (1H), 8.30 d (1H), 8.05 d (1H), 7.7–7.9 m (1H), 6.52 t (1H), 3.17 qua (2H), 2.94 s (6H), 1.43 qui (2H), 1.25 sext (2H), 0.85 t (3H).

b) 2-[N,N-(Dimethylamino)sulfonyl]benzenesulfonyl isocyanate

The sulfonylurea obtained in a) was converted into the corresponding sulfonyl isocyanate similarly to the preparation of 2-(methylsulfynyl)benzenesulfonyl isocyanate.

IV. Preparation of the sulfonylurea compounds I

Example IV.1

N-[(4-Fluoro-6-trifluoromethoxy-1,3-pyrimidin-2-yl)aminocarbonyl]-
2-(ethylsulfonyl)benzenesulfonamide 4.1 g (0.015 mol) of 2-(ethylsulfonyl)benzenesulfonyl isocyanate in 40 ml of 1,2-dichloroethane were added to 2-amino-4-fluoro-6-trifluoromethoxypyrimidine in 100 ml of 1,2-dichloroethane at 25° C. while stirring in the course of 15 minutes, and stirring was continued for 12 hours. The reaction mixture was evaporated down under reduced pressure and the residue was stirred with methyl tert-butyl ether, filtered off under suction, washed and dried. 5.5 g (78% of theory) of the title compound were obtained as colorless crystals of melting point 160° C. (decomposition).

(Active ingredient Example 1.003) Example IV.2

Sodium salt of
N-[(4-fluoro-6-trifluoromethoxy-1,3-pyrimidin-2-yl)aminocarbonyl]-
2-(ethylsulfonyl)benzenesulfonamide 0.88 g (0.0049 mol) of 30% strength sodium methylate solution was added at 0° C., while stirring, to a suspension of 2.3 g (0.0049 mol) of the compound from Example IV.1 and stirring was continued for 30 minutes at 0° C. Evaporating down under reduced pressure, stirring the residue with methyl tert-butyl ether, washing and drying gave the title compound as colorless crystals of melting point 133° C. (decomposition).

(Active ingredient example 1.021) Example IV.3

2-[[(4-Fluoro-6-trifluoromethoxypyrimidin-2-yl)aminocarbonyl]aminosulfonyl]benzenesulfonic acid N,N-dimethylamide 5.9 g (20 mmol) of 2-(dimethylamino)sulfonylbenzenesulfonyl isocyanate were added to a solution of 4.0 g (20 mmol) of 2-amino-4-fluoro-6-trifluoromethoxypyrimidine in 30 ml of methylene chloride at 25° C. Stirring was carried out for 16 hours at 25° C., and the product which separated out was filtered off under suction, washed with a little ether and dried at 50° C. under reduced pressure from a water pump. 2.1 g of the title compound (22% of theory) of melting point 167°–169° C. were obtained in this manner. Further product can be isolated from the mother liquor. (Active ingredient example 15.001) Example IV. 4

N-[(4-Methoxy-6-trifluoromethoxypyrimidin-2-yl) aminocarbonyl]-2-methylsulfynylbenzenesulfonamide 4.7 g (19 mmol) of 2-(methylsulfynyl)benzenesulfonyl isocyanate were added to a solution of 4.0 g (19 mmol) of 2-amino-4-methoxy-6-trifluoromethoxypyrimidine in 30 ml of methylene chloride at 25° C. Stirring was carried out for 16 hours at 25° C., and the product which separated out was filtered off under suction, washed with a little ether and dried at 50° C. under reduced pressure from a water pump. 0.9 g of the title compound (10% of theory) of melting point 110°–116° C. were obtained in this manner. Further product can be isolated from the mother liquor.
(Active ingredient example 14.007)

TABLE 1

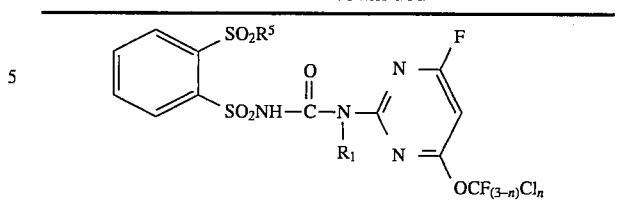

| No. | R¹ | R⁵ | n | Mp. (°C.) | |
|---|---|---|---|---|---|
| 1.001 | H | CH₃ | 0 | | |
| 1.002 | CH₃ | CH₃ | 0 | | |
| 1.003 | H | CH₂CH₃ | 0 | 160 decomp. | |
| 1.004 | CH₃ | CH₂CH₃ | 0 | | |
| 1.005 | H | (CH₂)₂CH₃ | 0 | 164 decomp. | |
| 1.006 | CH₃ | (CH₂)₂CH₃ | 0 | | |
| 1.007 | H | CH(CH₃)₂ | 0 | 198–199 | |
| 1.008 | H | CH₂—CH=CH₂ | 0 | | |
| 1.009 | H | CH₂—CH=CH—CH₃ | 0 | | |
| 1.010 | H | CH₂—C≡C—CH₃ | 0 | | |
| 1.011 | H | (CH₂)₂Cl | 0 | | |
| 1.012 | CH₃ | (CH₂)₂Cl | 0 | | |
| 1.013 | H | (CH₂)₂OCH₃ | 0 | | |
| 1.014 | H | (CH₂)₂O(CH₂)₂OCH₃ | 0 | | |
| 1.015 | H | Cyclopentyl | 0 | | |
| 1.016 | H | Cyclohexyl | 0 | | |
| 1.017 | H | CH₂CF₃ | 0 | | |
| 1.018 | H | CH=CH₂ | 0 | | |
| 1.019 | H | CH₃ | 0 | | Na salt |
| 1.020 | CH₃ | CH₃ | 0 | | Na salt |
| 1.021 | H | CH₂CH₃ | 0 | 133 decomp. | Na salt |
| 1.022 | CH₃ | CH₂CH₃ | 0 | | Na salt |
| 1.023 | H | (CH₂)₂CH₃ | 0 | 150 decomp. | Na salt |
| 1.024 | H | (CH₂)₂Cl | 0 | | Na salt |
| 1.025 | H | CH(CH₃)₂ | 0 | 169 decomp. | Na salt |

TABLE 2

| No. | R¹ | R⁵ | n | Mp. (°C.) | |
|---|---|---|---|---|---|
| 2.001 | H | CH₃ | 1 | | |
| 2.002 | CH₃ | CH₃ | 1 | | |
| 2.003 | H | CH₂CH₃ | 1 | | |
| 2.004 | CH₃ | CH₂CH₃ | 1 | | |
| 2.005 | H | (CH₂)₂CH₃ | 1 | 169–172 decomp. | |
| 2.006 | CH₃ | (CH₂)₂CH₃ | 1 | | |
| 2.007 | H | CH(CH₃)₂ | 1 | | |
| 2.008 | H | CH₂—CH=CH₂ | 1 | | |
| 2.009 | H | CH₂—CH=CH—CH₃ | 1 | | |
| 2.010 | H | CH₂—C≡C—CH₃ | 1 | | |
| 2.011 | H | (CH₂)₂Cl | 1 | | |
| 2.012 | CH₃ | (CH₂)₂Cl | 1 | | |
| 2.013 | H | (CH₂)₂OCH₃ | 1 | | |
| 2.014 | H | (CH₂)₂O(CH₂)₂OCH₃ | 1 | | |
| 2.015 | H | Cyclopentyl | 1 | | |
| 2.016 | H | Cyclohexyl | 1 | | |
| 2.017 | H | CH₂CF₃ | 1 | | |
| 2.018 | H | CH=CH₂ | 1 | | |
| 2.019 | H | CH₃ | 1 | | Na salt |
| 2.020 | CH₃ | CH₃ | 1 | | Na salt |
| 2.021 | H | CH₂CH₃ | 1 | | Na salt |
| 2.022 | CH₃ | CH₂CH₃ | 1 | | Na salt |
| 2.023 | H | (CH₂)₂CH₃ | 1 | 138 decomp. | Na salt |
| 2.024 | H | (CH₂)₂Cl | 1 | | Na salt |

TABLE 3

| No. | R¹ | R⁵ | n | Mp. (°C.) | |
|---|---|---|---|---|---|
| 3.001 | H | CH₃ | 0 | | |
| 3.002 | CH₃ | CH₃ | 0 | | |
| 3.003 | H | CH₂CH₃ | 0 | 173–178 | |
| 3.004 | CH₃ | CH₂CH₃ | 0 | | |
| 3.005 | H | (CH₂)₂CH₃ | 0 | | |
| 3.006 | CH₃ | (CH₂)₂CH₃ | 0 | | |
| 3.007 | H | CH(CH₃)₂ | 0 | | |
| 3.008 | H | CH₂—CH=CH₂ | 0 | | |
| 3.009 | H | CH₂—CH=CH—CH₃ | 0 | | |
| 3.010 | H | CH₂—C≡C—CH₃ | 0 | | |
| 3.011 | H | (CH₂)₂Cl | 0 | | |
| 3.012 | CH₃ | (CH₂)₂Cl | 0 | | |
| 3.013 | H | (CH₂)₂OCH₃ | 0 | | |
| 3.014 | H | (CH₂)₂O(CH₂)₂OCH₃ | 0 | | |
| 3.015 | H | Cyclopentyl | 0 | | |
| 3.016 | H | Cyclohexyl | 0 | | |
| 3.017 | H | CH₂CF₃ | 0 | | |
| 3.018 | H | CH=CH₂ | 0 | | |
| 3.019 | H | CH₃ | 0 | | Na salt |
| 3.020 | CH₃ | CH₃ | 0 | | Na salt |
| 3.021 | H | CH₂CH₃ | 0 | 130 decomp. | Na salt |
| 3.022 | CH₃ | CH₂CH₃ | 0 | | Na salt |
| 3.023 | H | (CH₂)₂CH₃ | 0 | | Na salt |
| 3.024 | H | (CH₂)₂Cl | 0 | | Na salt |

TABLE 4

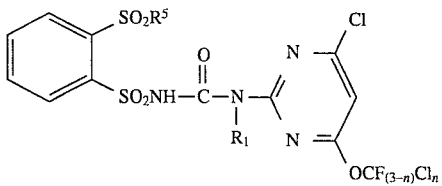

| No. | $R^1$ | $R^5$ | n | Mp. (°C.) |
|---|---|---|---|---|
| 4.001 | H | $CH_3$ | 1 | |
| 4.002 | $CH_3$ | $CH_3$ | 1 | |
| 4.003 | H | $CH_2CH_3$ | 1 | |
| 4.004 | $CH_3$ | $CH_2CH_3$ | 1 | |
| 4.005 | H | $(CH_2)_2CH_3$ | 1 | |
| 4.006 | $CH_3$ | $(CH_2)_2CH_3$ | 1 | |
| 4.007 | H | $CH(CH_3)_2$ | 1 | |
| 4.008 | H | $CH_2-CH=CH_2$ | 1 | |
| 4.009 | H | $CH_2-CH=CH-CH_3$ | 1 | |
| 4.010 | H | $CH_2-C\equiv C-CH_3$ | 1 | |
| 4.011 | H | $(CH_2)_2Cl$ | 1 | |
| 4.012 | $CH_3$ | $(CH_2)_2Cl$ | 1 | |
| 4.013 | H | $(CH_2)_2OCH_3$ | 1 | |
| 4.014 | H | $(CH_2)_2O(CH_2)_2OCH_3$ | 1 | |
| 4.015 | H | Cyclopentyl | 1 | |
| 4.016 | H | Cyclohexyl | 1 | |
| 4.017 | H | $CH_2CF_3$ | 1 | |
| 4.018 | H | $CH=CH_2$ | 1 | |
| 4.019 | H | $CH_3$ | 1 | Na salt |
| 4.020 | $CH_3$ | $CH_3$ | 1 | Na salt |
| 4.021 | H | $CH_2CH_3$ | 1 | Na salt |
| 4.022 | $CH_3$ | $CH_2CH_3$ | 1 | Na salt |
| 4.023 | H | $(CH_2)_2CH_3$ | 1 | Na salt |
| 4.024 | H | $(CH_2)_2Cl$ | 1 | Na salt |

TABLE 5

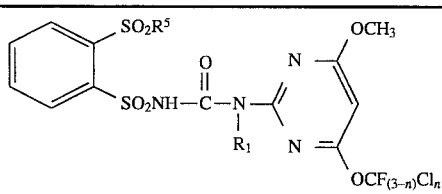

| No. | $R^1$ | $R^5$ | n | Mp. (°C.) | |
|---|---|---|---|---|---|
| 5.001 | H | $CH_3$ | 0 | 193–196 | |
| 5.002 | $CH_3$ | $CH_3$ | 0 | | |
| 5.003 | H | $CH_2CH_3$ | 0 | 154–157 | |
| 5.004 | $CH_3$ | $CH_2CH_3$ | 0 | | |
| 5.005 | H | $(CH_2)_2CH_3$ | 0 | 189–192 decomp. | |
| 5.006 | $CH_3$ | $(CH_2)_2CH_3$ | 0 | | |
| 5.007 | H | $CH(CH_3)_2$ | 0 | 138–143 decomp. | |
| 5.008 | H | $CH_2-CH=CH_2$ | 0 | | |
| 5.009 | H | $CH_2-CH=CH-CH_3$ | 0 | | |
| 5.010 | H | $CH_2-C\equiv C-CH_3$ | 0 | | |
| 5.011 | H | $(CH_2)_2Cl$ | 0 | | |
| 5.012 | $CH_3$ | $(CH_2)_2Cl$ | 0 | | |
| 5.013 | H | $(CH_2)_2OCH_3$ | 0 | | |
| 5.014 | H | $(CH_2)_2O(CH_2)_2OCH_3$ | 0 | | |
| 5.015 | H | Cyclopentyl | 0 | | |
| 5.016 | H | Cyclohexyl | 0 | | |
| 5.017 | H | $CH_2CF_3$ | 0 | | |
| 5.018 | H | $CH=CH_2$ | 0 | | |
| 5.019 | H | $CH_3$ | 0 | | Na salt |
| 5.020 | $CH_3$ | $CH_3$ | 0 | | Na salt |
| 5.021 | H | $CH_2CH_3$ | 0 | 170 decomp. | Na salt |
| 5.022 | $CH_3$ | $CH_2CH_3$ | 0 | | Na salt |
| 5.023 | H | $(CH_2)_2CH_3$ | 0 | 167 decomp. | Na salt |
| 5.024 | H | $(CH_2)_2Cl$ | 0 | | Na salt |

TABLE 6

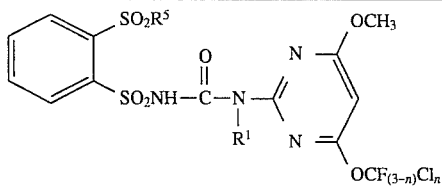

| No | $R^1$ | $R^5$ | n | Mp. (°C.) | |
|---|---|---|---|---|---|
| 6.001 | H | $CH_3$ | 1 | 178–180 | |
| 6.002 | $CH_3$ | $CH_3$ | 1 | | |
| 6.003 | H | $CH_2CH_3$ | 1 | | |
| 6.004 | $CH_3$ | $CH_2CH_3$ | 1 | | |
| 6.005 | H | $(CH_2)_2CH_3$ | 1 | 172–177 decomp. | |
| 6.006 | $CH_3$ | $(CH_2)_2CH_3$ | 1 | | |
| 6.007 | H | $CH(CH_3)_2$ | 1 | | |
| 6.008 | H | $CH_2-CH=CH_2$ | 1 | | |
| 6.009 | H | $CH_2-CH=CH-CH_3$ | 1 | | |
| 6.010 | H | $CH_2-C\equiv C-CH_3$ | 1 | | |
| 6.011 | H | $(CH_2)_2Cl$ | 1 | | |
| 6.012 | $CH_3$ | $(CH_2)_2Cl$ | 1 | | |
| 6.013 | H | $(CH_2)_2OCH_3$ | 1 | | |
| 6.014 | H | $(CH_2)_2O(CH_2)_2OCH_3$ | 1 | | |
| 6.015 | H | Cyclopentyl | 1 | | |
| 6.016 | H | Cyclohexyl | 1 | | |
| 6.017 | H | $CH_2CF_3$ | 1 | | |
| 6.018 | H | $CH=CH_2$ | 1 | | |
| 6.019 | H | $CH_3$ | 1 | | Na salt |
| 6.020 | $CH_3$ | $CH_3$ | 1 | | Na salt |
| 6.021 | H | $CH_2CH_3$ | 1 | | Na salt |
| 6.022 | $CH_3$ | $CH_2CH_3$ | 1 | | Na salt |
| 6.023 | H | $(CH_2)_2CH_3$ | 1 | 181 decomp. | Na salt |
| 6.024 | H | $(CH_2)_2Cl$ | 1 | | Na salt |

TABLE 7

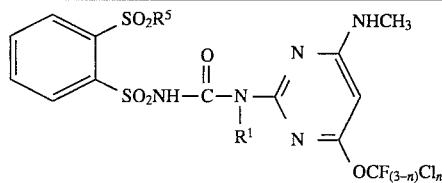

| No. | $R^1$ | $R^5$ | n | Mp. (°C.) | |
|---|---|---|---|---|---|
| 7.001 | H | $CH_3$ | 0 | | |
| 7.002 | $CH_3$ | $CH_3$ | 0 | | |
| 7.003 | H | $CH_2CH_3$ | 0 | 127 | |
| 7.004 | $CH_3$ | $CH_2CH_3$ | 0 | | |
| 7.005 | H | $(CH_2)_2CH_3$ | 0 | 154 | |
| 7.006 | $CH_3$ | $(CH_2)_2CH_3$ | 0 | | |
| 7.007 | H | $CH(CH_3)_2$ | 0 | | |
| 7.008 | H | $CH_2-CH=CH_2$ | 0 | | |
| 7.009 | H | $CH_2-CH=CH-CH_3$ | 0 | | |
| 7.010 | H | $CH_2-C\equiv C-CH_3$ | 0 | | |
| 7.011 | H | $(CH_2)_2Cl$ | 0 | | |
| 7.012 | $CH_3$ | $(CH_2)_2Cl$ | 0 | | |
| 7.013 | H | $(CH_2)_2OCH_3$ | 0 | | |
| 7.014 | H | $(CH_2)_2O(CH_2)_2OCH_3$ | 0 | | |
| 7.015 | H | Cyclopentyl | 0 | | |
| 7.016 | H | Cyclohexyl | 0 | | |
| 7.017 | H | $CH_2CF_3$ | 0 | | |
| 7.018 | H | $CH=CH_2$ | 0 | | |
| 7.019 | H | $CH_3$ | 0 | | Na salt |
| 7.020 | $CH_3$ | $CH_3$ | 0 | | Na salt |
| 7.021 | H | $CH_2CH_3$ | 0 | 192 decomp. | Na salt |

TABLE 7-continued

Structure: benzene ring with SO₂R⁵ and SO₂NH-C(=O)-N(R¹)-[pyrimidine with NHCH₃ and OCF$_{(3-n)}$Cl$_n$]

| No. | R¹ | R⁵ | n | Mp. (°C.) | |
|---|---|---|---|---|---|
| 7.022 | CH₃ | CH₂CH₃ | 0 | | Na salt |
| 7.023 | H | (CH₂)₂CH₃ | 0 | 181 decomp. | Na salt |
| 7.024 | H | (CH₂)₂Cl | 0 | | Na salt |

TABLE 8

Structure: benzene ring with SO₂R⁵ and SO₂NH-C(=O)-N(R¹)-[pyrimidine with NHCH₃ and OCF$_{(3-n)}$Cl$_n$]

| No. | R¹ | R⁵ | n | Mp. (°C.) | |
|---|---|---|---|---|---|
| 8.001 | H | CH₃ | 1 | | |
| 8.002 | CH₃ | CH₃ | 1 | | |
| 8.003 | H | CH₂CH₃ | 1 | | |
| 8.004 | CH₃ | CH₂CH₃ | 1 | | |
| 8.005 | H | (CH₂)₂CH₃ | 1 | | |
| 8.006 | CH₃ | (CH₂)₂CH₃ | 1 | | |
| 8.007 | H | CH(CH₃)₂ | 1 | | |
| 8.008 | H | CH₂—CH=CH₂ | 1 | | |
| 8.009 | H | CH₂—CH=CH—CH₃ | 1 | | |
| 8.010 | H | CH₂—C≡C—CH₃ | 1 | | |
| 8.011 | H | (CH₂)₂Cl | 1 | | |
| 8.012 | CH₃ | (CH₂)₂Cl | 1 | | |
| 8.013 | H | (CH₂)₂OCH₃ | 1 | | |
| 8.014 | H | (CH₂)₂O(CH₂)₂OCH₃ | 1 | | |
| 8.015 | H | Cyclopentyl | 1 | | |
| 8.016 | H | Cyclohexyl | 1 | | |
| 8.017 | H | CH₂CF₃ | 1 | | |
| 8.018 | H | CH=CH₂ | 1 | | |
| 8.019 | H | CH₃ | 1 | | Na salt |
| 8.020 | CH₃ | C₃ | 1 | | Na salt |
| 8.021 | H | CH₂CH₃ | 1 | | Na salt |
| 8.022 | CH₃ | CH₂CH₃ | 1 | | Na salt |
| 8.023 | H | (CH₂)₂CH₃ | 1 | | Na salt |
| 8.024 | H | (CH₂)₂Cl | 1 | | Na salt |

TABLE 9

Structure: benzene ring with NO₂ and SO₂NH-C(=O)-N(R¹)-[pyrimidine with X-R² and OCF$_{(3-n)}$Cl$_n$]

| No. | R¹ | X | R² | n | Mp. (°C.) | |
|---|---|---|---|---|---|---|
| 9.001 | H | — | F | 0 | 148–154 | |
| 9.002 | H | — | Cl | 0 | | |
| 9.003 | CH₃ | — | F | 0 | | |
| 9.004 | CH₃ | — | Cl | 0 | | |
| 9.005 | H | — | F | 1 | 153–160 decomp. | |
| 9.006 | H | — | Cl | 1 | | |
| 9.007 | CH₃ | — | F | 1 | | |
| 9.008 | CH₃ | — | Cl | 1 | | |
| 9.009 | H | — | F | 0 | 140 decomp. | Na salt |
| 9.010 | H | — | Cl | 0 | | Na salt |
| 9.011 | H | O | CH₃ | 0 | 189–191 | |
| 9.012 | H | O | CH₃ | 1 | 149–152 | |
| 9.013 | CH₃ | O | CH₃ | 0 | 93–96 | |
| 9.014 | CH₃ | O | CH₃ | 1 | | |
| 9.015 | CH₃ | O | CH₃ | 0 | 192 decomp. | Na salt |
| 9.016 | CH₃ | O | CH₃ | 1 | | Na salt |
| 9.017 | H | NH | CH₃ | 0 | 211 decomp. | |
| 9.018 | H | NH | CH₃ | 1 | | |
| 9.019 | H | NCH₃ | CH₃ | 0 | 193–196 decomp. | |
| 9.020 | H | NCH₃ | CH₃ | 1 | | |
| 9.021 | CH₃ | NH | CH₃ | 0 | | |
| 9.022 | H | O | CH₃ | 0 | 155 decomp. | Na salt |
| 9.023 | H | — | F | 1 | 130 decomp. | Na salt |
| 9.024 | H | NCH₃ | CH₃ | 0 | | |
| 9.025 | H | NCH₃ | CH₃ | 0 | 152–158 | Na salt |
| 9.026 | H | NH | CH₃ | 0 | 165 decomp. | Na salt |
| 9.027 | H | O | CH₃ | 1 | 151 decomp. | Na salt |

TABLE 10

Structure: benzene ring with O—CH₂CH₂OCH₃ and SO₂NH-C(=O)-N(R¹)-[pyrimidine with X-R² and OCF$_{(3-n)}$Cl$_n$]

| No. | R¹ | X | R² | n | Mp. (°C.) | |
|---|---|---|---|---|---|---|
| 10.001 | H | — | F | 0 | 132–135 | |
| 10.002 | H | — | Cl | 0 | | |
| 10.003 | H | — | F | 1 | 125–128 | |
| 10.004 | H | — | Cl | 1 | | |
| 10.005 | H | O | CH₃ | 0 | 131–135 | |
| 10.006 | H | O | CH₃ | 1 | 148–150 | |
| 10.007 | H | NH | CH₃ | 0 | | |
| 10.008 | H | NH | CH₃ | 1 | | |
| 10.009 | CH₃ | NH | CH₃ | 0 | | |
| 10.010 | CH₃ | NH | CH₃ | 1 | | |
| 10.011 | H | O | CH₃ | 0 | | Na salt |
| 10.012 | H | — | F | 0 | 175–180 decomp. | Na salt |
| 10.013 | H | O | CH₃ | 1 | 255 decomp. | Na salt |
| 10.014 | H | O | C₂H₅ | 0 | 142–144 | |
| 10.015 | H | O | C₂H₅ | 1 | 121–123 | |
| 10.016 | H | NH | CH₃ | 0 | | Na salt |
| 10.017 | H | NH | CH₃ | 1 | | Na salt |
| 10.018 | H | NCH₃ | CH₃ | 0 | | |
| 10.019 | H | NCH₃ | CH₃ | 0 | | Na salt |
| 10.020 | H | NCH₃ | CH₃ | 1 | | |
| 10.021 | H | NCH₃ | CH₃ | 1 | | Na salt |

TABLE 11

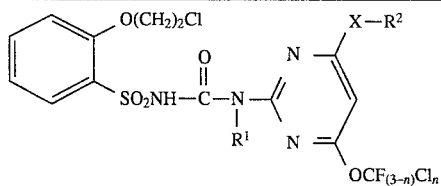

| No. | R¹ | X | R² | n | Mp. (°C.) | |
|---|---|---|---|---|---|---|
| 11.001 | H | — | F | 0 | | |
| 11.002 | H | — | Cl | 0 | | |
| 11.003 | H | — | F | 1 | | |
| 11.004 | H | — | Cl | 1 | | |
| 11.005 | H | O | $CH_3$ | 0 | 147–150 | |
| 11.006 | H | O | $CH_3$ | 1 | 141–143 | |
| 11.007 | H | NH | $CH_3$ | 0 | | |
| 11.008 | H | NH | $CH_3$ | 1 | | |
| 11.009 | $CH_3$ | NH | $CH_3$ | 0 | | |
| 11.010 | $CH_3$ | NH | $CH_3$ | 1 | | |
| 11.011 | H | O | $CH_3$ | 0 | | Na salt |
| 11.012 | H | — | F | 0 | | Na salt |
| 11.013 | H | O | $CH_3$ | 1 | | Na salt |
| 11.014 | H | NH | $CH_3$ | 0 | | Na salt |
| 11.015 | H | NH | $CH_3$ | 1 | | Na salt |
| 11.016 | H | $NCH_3$ | $CH_3$ | 0 | 203–205 | |
| 11.017 | H | $NCH_3$ | $CH_3$ | 0 | 135–140 | Na salt |
| 11.018 | H | $NCH_3$ | $CH_3$ | 1 | | |
| 11.019 | H | $NCH_3$ | $CH_3$ | 1 | | Na salt |

TABLE 12

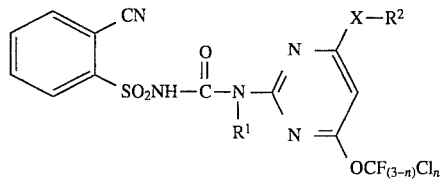

| No. | R¹ | X | R² | n | Mp. (°C.) | |
|---|---|---|---|---|---|---|
| 12.001 | H | — | F | 0 | | |
| 12.002 | H | — | Cl | 0 | | |
| 12.003 | H | — | F | 1 | | |
| 12.004 | H | — | Cl | 1 | | |
| 12.005 | H | O | $CH_3$ | 0 | | |
| 12.006 | H | O | $CH_3$ | 1 | | |
| 12.007 | H | NH | $CH_3$ | 0 | | |
| 12.008 | H | NH | $CH_3$ | 1 | | |
| 12.009 | $CH_3$ | NH | $CH_3$ | 0 | | |
| 12.010 | $CH_3$ | NH | $CH_3$ | 1 | | Na salt |
| 12.011 | H | O | $CH_3$ | 0 | | Na salt |
| 12.012 | H | — | F | 0 | | |
| 12.013 | H | O | $CH_3$ | 1 | | Na salt |
| 12.014 | H | NH | $CH_3$ | 0 | | Na salt |
| 12.015 | H | NH | $CH_3$ | 1 | | Na salt |
| 12.016 | H | $NCH_3$ | $CH_3$ | 0 | | |
| 12.017 | H | $NCH_3$ | $CH_3$ | 0 | | Na salt |
| 12.018 | H | $NCH_3$ | $CH_3$ | 1 | | |
| 12.019 | H | $NCH_3$ | $CH_3$ | 1 | | Na salt |

TABLE 13

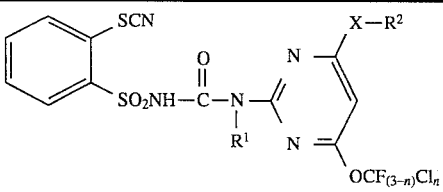

| No. | R¹ | X | R² | n | Mp. (°C.) | |
|---|---|---|---|---|---|---|
| 13.001 | H | — | F | 0 | | |
| 13.002 | H | — | Cl | 0 | | |
| 13.003 | H | — | F | 1 | | |
| 13.004 | H | — | Cl | 1 | | |
| 13.005 | H | O | $CH_3$ | 0 | | |
| 13.006 | H | O | $CH_3$ | 1 | | |
| 13.007 | H | NH | $CH_3$ | 0 | | |
| 13.008 | H | NH | $CH_3$ | 1 | | |
| 13.009 | $CH_3$ | NH | $CH_3$ | 0 | | |
| 13.010 | $CH_3$ | NH | $CH_3$ | 1 | | Na salt |
| 13.011 | H | O | $CH_3$ | 0 | | Na salt |
| 13.012 | H | — | F | 0 | | |
| 13.013 | H | O | $CH_3$ | 1 | | Na salt |
| 13.014 | H | NH | $CH_3$ | 0 | | Na salt |
| 13.015 | H | NH | $CH_3$ | 1 | | Na salt |
| 13.016 | H | $NCH_3$ | $CH_3$ | 0 | | |
| 13.017 | H | $NCH_3$ | $CH_3$ | 0 | | Na salt |
| 13.018 | H | $NCH_3$ | $CH_3$ | 1 | | |
| 13.019 | H | $NCH_3$ | $CH_3$ | 1 | | Na salt |

TABLE 14

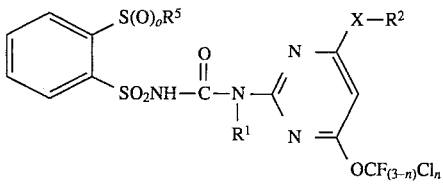

| No. | R¹ | R⁵ | X | R² | n | O | Mp. (°C.) | |
|---|---|---|---|---|---|---|---|---|
| 14.001 | H | $CH_3$ | — | F | 0 | 1 | | |
| 14.002 | H | $CH_3$ | — | F | 0 | 1 | | Na salt |
| 14.003 | H | $C_2H_5$ | — | F | 0 | 1 | | |
| 14.004 | H | $C_2H_5$ | — | F | 0 | 1 | | Na salt |
| 14.005 | H | $n-C_3H_7$ | — | F | 0 | 1 | | |
| 14.006 | H | $n-C_3H_7$ | — | F | 0 | 1 | | Na salt |
| 14.007 | H | $CH_3$ | O | $CH_3$ | 0 | 1 | 110–116 | |
| 14.008 | H | $CH_3$ | O | $CH_3$ | 0 | 1 | 150–151 (decomp.) | Na salt |
| 14.009 | H | $C_2H_5$ | O | $CH_3$ | 0 | 0 | | |
| 14.010 | H | $C_2H_5$ | O | $CH_3$ | 0 | 0 | | Na salt |
| 14.011 | H | $n-C_3H_7$ | O | $CH_3$ | 0 | 1 | | |
| 14.012 | H | $n-C_3H_7$ | O | $CH_3$ | 0 | 1 | | Na salt |
| 14.013 | H | $i-C_3H_7$ | O | $CH_3$ | 0 | 1 | | |
| 14.014 | H | $i-C_3H_7$ | O | $CH_3$ | 0 | 1 | | Na salt |
| 14.015 | H | $C_2H_5$ | O | $CH_3$ | 0 | 1 | | |
| 14.016 | H | $C_2H_5$ | O | $CH_3$ | 0 | 1 | | |
| 14.017 | H | $C_2H_5$ | O | $CH_3$ | 1 | 1 | | |
| 14.018 | H | $C_2H_5$ | O | $CH_3$ | 1 | 1 | | Na salt |
| 14.019 | H | $n-C_3H_7$ | O | $CH_3$ | 1 | 1 | | |
| 14.020 | H | $n-C_3H_7$ | O | $CH_3$ | 1 | 1 | | Na salt |
| 14.021 | $CH_3$ | $C_2H_5$ | O | $CH_3$ | 0 | 1 | | |
| 14.022 | N | $C_2H_5$ | NH | $CH_3$ | 0 | 1 | | |
| 14.023 | H | $C_2H_5$ | NH | $CH_3$ | 0 | 1 | | Na salt |
| 14.024 | H | $C_2H_5$ | $NCH_3$ | $CH_3$ | 0 | 1 | | |
| 14.025 | H | $C_2H_5$ | $NCH_3$ | $CH_3$ | 0 | 2 | 198–202 | |
| 14.026 | H | $C_2H_5$ | $NCH_3$ | $CH_3$ | 0 | 2 | 169 decomp. | Na salt |
| 14.027 | H | $CH_3$ | O | $CH_3$ | 0 | 0 | 141–144 | |

TABLE 15

Structure: benzene with SO2N(CH3)2 (ortho) and SO2NH-C(=O)-N(R1)-[pyrimidine with X-R2 and OCF(3-n)Cl_n]

| No. | R1 | X | R2 | n | Mp. (°C.) | |
|---|---|---|---|---|---|---|
| 15.001 | H | — | F | | 167–169 | |
| 15.002 | H | — | Cl | 0 | | |
| 15.003 | H | — | F | 1 | | |
| 15.004 | H | — | Cl | 1 | | |
| 15.005 | H | O | CH3 | 0 | 160–163 | |
| 15.006 | H | O | CH3 | 1 | 145–150 | |
| 15.007 | H | NH | CH3 | 0 | | |
| 15.008 | H | NH | CH3 | 1 | | |
| 15.009 | CH3 | NH | CH3 | 0 | | |
| 15.010 | CH3 | NH | CH3 | 1 | | |
| 15.011 | H | O | CH3 | 0 | 165–177 | Na salt |
| 15.012 | H | — | F | 0 | 127–133 (decomp.) | Na salt |
| 15.013 | H | O | CH3 | 1 | | Na salt |
| 15.014 | H | NH | CH3 | 0 | | Na salt |
| 15.015 | H | NH | CH3 | 1 | | Na salt |
| 15.016 | H | NCH3 | CH3 | 0 | | |
| 15.017 | H | NCH3 | CH3 | 0 | | Na salt |
| 15.018 | H | NCH3 | CH3 | 1 | | |
| 15.019 | H | NCH3 | CH3 | 1 | | Na salt |
| 15.020 | H | O | CH3 | 0 | 178–186 (decomp.) | K salt |

TABLE 16

Structure: benzene with OCHF2 (ortho) and SO2NH-C(=O)-N(R1)-[pyrimidine with X-R2 and OCF(3-n)Cl_n]

| No. | R1 | X | R2 | n | Mp. (°C.) | |
|---|---|---|---|---|---|---|
| 16.001 | H | — | F | 0 | | |
| 16.002 | H | — | Cl | 0 | | |
| 16.003 | H | — | F | 1 | | |
| 16.004 | H | — | Cl | 1 | | |
| 16.005 | H | O | CH3 | 0 | 99–100 | |
| 16.006 | H | O | CH3 | 1 | | |
| 16.007 | H | NH | CH3 | 0 | | |
| 16.008 | CH3 | NH | CH3 | 1 | | |
| 16.009 | CH3 | NH | CH3 | 0 | | |
| 16.010 | CH3 | NH | CH3 | 1 | | Na salt |
| 16.011 | H | O | CH3 | 0 | 145–152 | Na salt |
| 16.012 | H | — | F | 0 | | |
| 16.013 | H | O | CH3 | 1 | | Na salt |
| 16.014 | H | NH | CH3 | 0 | | Na salt |
| 16.015 | H | NH | CH3 | 1 | | Na salt |
| 16.016 | H | NCH3 | CH3 | 0 | | |
| 16.017 | H | NCH3 | CH3 | 0 | | Na salt |
| 16.018 | H | NCH3 | CH3 | 1 | | |
| 16.019 | H | NCH3 | CH3 | 1 | | Na salt |

TABLE 17

Structure: substituted benzene (positions 1-6) with A at position 2, R3 substituent, and SO2NH-C(=O)-N(R1)-[pyrimidine with X-R2 and OCF(3-n)Cl_n]

| No. | A | R3 | R1 | X | R2 | n | Mp. (°C.) | |
|---|---|---|---|---|---|---|---|---|
| 17.001 | OCH3 | H | H | O | CH3 | 0 | 125–129 | |
| 17.002 | OCH3 | H | H | O | CH3 | 0 | 163 decomp. | Na salt |
| 17.003 | CH2OCH3 | H | H | O | CH3 | 0 | 135 | |
| 17.004 | N(CH3)SO2CH3 | H | H | O | CH3 | 0 | 214–216 | |
| 17.005 | N(CH3)SO2CH3 | H | H | O | CH3 | 0 | 171 decomp. | Na salt |
| 17.006 | OCH3 | 5-Cl | H | O | CH3 | 0 | | |
| 17.007 | SO2C2H5 | 5-Cl | H | O | CH3 | 0 | 152–156 | |
| 17.008 | SO2C2H5 | 5-Cl | H | O | CH3 | 1 | 143–148 | |
| 17.009 | SO2C2H5 | 5-OCH3 | H | O | CH3 | 0 | | |
| 17.010 | SO2C2H5 | 5-OCH3 | H | O | CH3 | 1 | | |
| 17.011 | OCH2CF3 | 5-OCH2CF3 | H | O | CH3 | 0 | 152–155 | |
| 17.012 | OCF2CF2H | H | H | O | CH3 | 0 | 151–153 | |
| 17.013 | OCF2CF2H | H | H | O | CH3 | 0 | 149 decomp. | Na salt |
| 17.014 | OCF2CFHCl | H | H | O | CH3 | 0 | 145–147 | |
| 17.015 | OCF2CFHCl | H | H | O | CH3 | 0 | 155 decomp. | Na salt |
| 17.016 | OCF2CF2H | H | H | O | CH3 | 1 | 128–130 | |
| 17.017 | OCF2CF2H | 5-Cl | H | O | CH3 | 0 | | |
| 17.018 | OCHF2 | 5-Cl | H | O | CH3 | 0 | | |
| 17.019 | OCF2CFHCl | 5-Cl | H | O | CH3 | 0 | 143–145 decomp. | |
| 17.020 | OCF2CFHCl | H | H | O | CH3 | 1 | | |
| 17.021 | SO2CH3 | 5-Cl | H | O | CH3 | 0 | | |
| 17.022 | SO2CH3 | 5-Cl | H | O | CH3 | 0 | | Na salt |
| 17.023 | SO2CH3 | 5-Cl | H | O | CH3 | 1 | | |

TABLE 17-continued

| No. | A | R³ | R¹ | X | R² | n | Mp. (°C.) | |
|---|---|---|---|---|---|---|---|---|
| 17.024 | SO₂CH₃ | 5-Cl | H | O | CH₃ | 1 | | Na salt |
| 17.025 | SO₂CH₃ | 6-Cl | H | O | CH₃ | 0 | | |
| 17.026 | SO₂CH₃ | 6-Cl | H | O | CH₃ | 0 | | Na salt |
| 17.027 | SO₂CH₃ | 6-Cl | H | O | CH₃ | 1 | | |
| 17.028 | SO₂CH₃ | 6-Cl | H | O | CH₃ | 1 | | Na salt |
| 17.029 | SO₂CH₃ | 5-CH₃ | H | O | CH₃ | 0 | | |
| 17.030 | SO₂CH₃ | 5-CH₃ | H | O | CH₃ | 0 | | Na salt |
| 17.031 | SO₂CH₃ | 5-CH₃ | H | O | CH₃ | 1 | | |
| 17.032 | SO₂CH₃ | 5-CH₃ | H | O | CH₃ | 1 | | Na salt |
| 17.033 | SO₂CH₃ | 6-CH₃ | H | O | CH₃ | 0 | | |
| 17.034 | SO₂CH₃ | 6-CH₃ | H | O | CH₃ | 0 | | Na salt |
| 17.035 | SO₂CH₃ | 6-CH₃ | H | O | CH₃ | 1 | | |
| 17.036 | SO₂CH₃ | 6-CH₃ | H | O | CH₃ | 1 | | Na salt |
| 17.037 | SO₂CH₃ | 5-OCH₃ | H | O | CH₃ | 0 | | |
| 17.038 | SO₂CH₃ | 5-OCH₃ | H | O | CH₃ | 0 | | Na salt |
| 17.039 | SO₂CH₃ | 5-OCH₃ | H | O | CH₃ | 1 | | |
| 17.040 | SO₂CH₃ | 5-OCH₃ | H | O | CH₃ | 1 | | Na salt |
| 17.041 | SO₂CH₃ | 6-OCH₃ | H | O | CH₃ | 0 | | |
| 17.042 | SO₂CH₃ | 6-OCH₃ | H | O | CH₃ | 0 | | Na salt |
| 17.043 | SO₂CH₃ | 6-OCH₃ | H | O | CH₃ | 1 | | |
| 17.045 | SO₂N(CH₃)₂ | 5-Cl | H | O | CH₃ | 0 | | |
| 17.046 | SO₂N(CH₃)₂ | 5-Cl | H | O | CH₃ | 0 | | Na salt |
| 17.047 | SO₂N(CH₃)₂ | 5-Cl | H | O | CH₃ | 1 | | |
| 17.048 | SO₂N(CH₃)₂ | 5-Cl | H | O | CH₃ | 1 | | Na salt |
| 17.049 | SO₂N(CH₃)₂ | 6-Cl | H | O | CH₃ | 0 | | |
| 17.050 | SO₂N(CH₃)₂ | 6-Cl | H | O | CH₃ | 0 | | Na salt |
| 17.051 | SO₂N(CH₃)₂ | 6-Cl | H | O | CH₃ | 1 | | |
| 17.052 | SO₂N(CH₃)₂ | 6-Cl | H | O | CH₃ | 1 | | Na salt |
| 17.053 | SO₂N(CH₃)₂ | 5-CH₃ | H | O | CH₃ | 0 | | |
| 17.054 | SO₂N(CH₃)₂ | 5-CH₃ | H | O | CH₃ | 0 | | Na salt |
| 17.055 | SO₂N(CH₃)₂ | 5-CH₃ | H | O | CH₃ | 1 | | |
| 17.056 | SO₂N(CH₃)₂ | 5-CH₃ | H | O | CH₃ | 1 | | Na salt |
| 17.057 | SO₂N(CH₃)₂ | 6-CH₃ | H | O | CH₃ | 0 | | |
| 17.058 | SO₂N(CH₃)₂ | 6-CH₃ | H | O | CH₃ | 0 | | Na salt |
| 17.059 | SO₂N(CH₃)₂ | 6-CH₃ | H | O | CH₃ | 1 | | |
| 17.060 | SO₂N(CH₃)₂ | 6-CH₃ | H | O | CH₃ | 1 | | Na salt |
| 17.061 | SO₂N(CH₃)₂ | 5-OCH₃ | H | O | CH₃ | 0 | | |
| 17.062 | SO₂N(CH₃)₂ | 5-OCH₃ | H | O | CH₃ | 0 | | Na salt |
| 17.063 | SO₂N(CH₃)₂ | 5-OCH₃ | H | O | CH₃ | 1 | | |
| 17.064 | SO₂N(CH₃)₂ | 5-OCH₃ | H | O | CH₃ | 1 | | Na salt |
| 17.065 | SO₂N(CH₃)₂ | 6-OCH₃ | H | O | CH₃ | 0 | | |
| 17.066 | SO₂N(CH₃)₂ | 6-OCH₃ | H | O | CH₃ | 0 | | Na salt |
| 17.067 | SO₂H(CH₃)₂ | 6-OCH₃ | H | O | CH₃ | 1 | | |
| 17.068 | SO₂N(CH₃)₂ | 6-OCH₃ | H | O | CH₃ | 1 | | Na salt |
| 17.069 | CH₂OCH₃ | H | H | O | CH₃ | 0 | | Na salt |
| 17.070 | CH₂OCH₃ | H | H | O | CH₃ | 1 | | |
| 17.071 | CH₂OCH₃ | H | H | O | CH₃ | 1 | | Na salt |
| 17.072 | CH=NOCH₃ | H | H | O | CH₃ | 0 | | |
| 17.073 | CH=NOCH₃ | H | H | O | CH₃ | 0 | | Na salt |
| 17.074 | CH=NOCH₃ | H | H | O | CH₃ | 1 | | |
| 17.075 | CH=NOCH₃ | H | H | O | CH₃ | 1 | | Na salt |
| 17.076 | CCl₃ | H | H | O | CH₃ | 0 | | |
| 17.077 | CCl₃ | H | H | O | CH₃ | 0 | | Na salt |
| 17.078 | CCl₃ | H | H | O | CH₃ | 1 | 195 | |
| 17.079 | CCl₃ | H | H | O | CH₃ | 1 | 125–130 (decomp.) | Na salt |
| 17.080 | OCF₃ | H | H | O | CH₃ | 0 | 127 | |
| 17.081 | OCF₃ | H | H | O | CH₃ | 0 | 119 (decomp.) | Na salt |
| 17.082 | OCF₃ | H | H | O | CH₃ | 1 | | |
| 17.083 | OCF₃ | H | H | O | CH₃ | 1 | | Na salt |
| 17.084 | CH₂OC₂H₅ | H | H | O | CH₃ | 0 | | |
| 17.085 | CH₂OC₂H₅ | H | H | O | CH₃ | 0 | | Na salt |
| 17.086 | CH₂OC₂H₅ | H | H | O | CH₃ | 1 | | |
| 17.087 | CH₂OC₂H₅ | H | H | O | CH₃ | 1 | | Na salt |
| 17.088 | O(C=O)CH₃ | H | H | O | CH₃ | 0 | | |
| 17.089 | O(C=O)CH₃ | H | H | O | CH₃ | 0 | | Na salt |

TABLE 17-continued $$\begin{array}{c}\text{structure with positions 1-6 on benzene ring, R}^3\text{ substituent, A at position 2,}\\ \text{SO}_2\text{NH-C(=O)-N(R}^1\text{)- linked to pyrimidine bearing X-R}^2\text{ and OCF}_{(3-n)}\text{Cl}_n\end{array}$$

| No. | A | R$^3$ | R$^1$ | X | R$^2$ | n | Mp. (°C.) | |
|---|---|---|---|---|---|---|---|---|
| 17.090 | O(C=O)CH$_3$ | H | H | O | CH$_3$ | 1 | | |
| 17.091 | O(C=O)CH$_3$ | H | H | O | CH$_3$ | 1 | | Na salt |
| 17.092 | O(C=O)OCH$_3$ | H | H | O | CH$_3$ | 0 | | |
| 17.093 | O(C=O)OCH$_3$ | H | H | O | CH$_3$ | 0 | | Na salt |
| 17.094 | O(C=O)OCH$_3$ | H | H | O | CH$_3$ | 1 | | |
| 17.095 | O(C=O)OCH$_3$ | H | H | O | CH$_3$ | 1 | | Na salt |
| 17.096 | N(CH$_3$)COCH$_3$ | H | H | O | CH$_3$ | 0 | | |
| 17.097 | N(CH$_3$)COCH$_3$ | H | H | O | CH$_3$ | 0 | | Na salt |
| 17.098 | N(CH$_3$)COCH$_3$ | H | H | O | CH$_3$ | 1 | | |
| 17.099 | N(CH$_3$)COCH$_3$ | H | H | O | CH$_3$ | 1 | | Na salt |
| 17.100 | H(CH$_3$)COCH$_2$Cl | H | H | O | CH$_3$ | 0 | | |
| 17.101 | N(CH$_3$)COCH$_2$Cl | H | H | O | CH$_3$ | 0 | | Na salt |
| 17.102 | N(CH$_3$)COCH$_2$Cl | H | H | O | CH$_3$ | 1 | | |
| 17.103 | N(CH$_3$)COCH$_2$Cl | H | H | O | CH$_3$ | 1 | | Na salt |
| 17.104 | N(CH$_3$)COCF$_3$ | H | H | O | CH$_3$ | 0 | | |
| 17.105 | N(CH$_3$)COCF$_3$ | H | H | O | CH$_3$ | 0 | | Na salt |
| 17.106 | H(CH$_3$)COCF$_3$ | H | H | O | CH$_3$ | 1 | | |
| 17.107 | N(CH$_3$)COCF$_3$ | H | H | O | CH$_3$ | 1 | | Na salt |
| 17.108 | N(CH$_3$)CON(CH$_3$)$_2$ | H | H | O | CH$_3$ | 0 | | |
| 17.109 | N(CH$_3$)CON(CH$_3$)$_2$ | H | H | O | CH$_3$ | 0 | | Na salt |
| 17.110 | N(CH$_3$)CON(CH$_3$)$_2$ | H | H | O | CH$_3$ | 1 | | |
| 17.111 | N(CH$_3$)CON(CH$_3$)$_2$ | H | H | O | CH$_3$ | 1 | | Na salt |
| 17.112 | O(C=O)N(CH$_3$)$_2$ | H | H | O | CH$_3$ | 0 | | |
| 17.113 | O(C=O)N(CH$_3$)$_2$ | H | H | O | CH$_3$ | 0 | | Na salt |
| 17.114 | O(C=O)N(CH$_3$)$_2$ | H | H | O | CH$_3$ | 1 | | |
| 17.115 | O(C=O)N(CH$_3$)$_2$ | H | H | O | CH$_3$ | 1 | | Na salt |
| 17.116 | NSO$_2$N(CH$_3$)$_2$ | H | H | O | CH$_3$ | 0 | | |
| 17.117 | NSO$_2$N(CH$_3$)$_2$ | H | H | O | CH$_3$ | 0 | | Na salt |
| 17.118 | NSO$_2$N(CH$_3$)$_2$ | H | H | O | CH$_3$ | 1 | | |
| 17.119 | NSO$_2$N(CH$_3$)$_2$ | H | H | O | CH$_3$ | 1 | | Na salt |
| 17.120 | CH$_3$ | H | H | O | CH$_3$ | 0 | 161–162 | |
| 17.121 | CH$_3$ | H | H | O | CH$_3$ | 0 | 168 decomp. | Na salt |
| 17.122 | OCH$_2$CF$_3$ | 5-OCH$_2$CF$_3$ | H | O | CH$_3$ | 0 | 207–210 decomp. | Na salt |
| 17.123 | OCH$_2$CN | H | H | O | CH$_3$ | 0 | 128 decomp. | |
| 17.124 | OCH$_2$CN | H | H | O | CH$_3$ | 1 | 135 decomp. | |

Use Examples

The herbicidal action of the sulfonylureas of the formula I could be demonstrated by greenhouse experiments:

The culture vessels used were plastic flowerpots containing loamy sand with about 3.0% of humus as a substrate. The seeds of the test plants were sown separately according to species.

In the pre-emergence treatment, the active ingredients suspended or emulsified in water were applied directly after sowing, by means of finely distributing nozzles. The vessels were lightly irrigated in order to promote germination and growth and then covered with transparent plastic covers until the plants had begun to grow. This covering promotes uniform germination of the test plants, unless this is impaired by the active ingredients.

For the purpose of the post-emergence treatment, the test plants were first grown to a height of growth of from 3 to 15 cm, depending on the form of growth, and then treated with the active ingredients suspended or emulsified in water. The application rate for the post-emergence treatment was 0.5 kg/ha of a.i.

The plants were kept at 10°–25° C. .or 20°–35° C., depending on the species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments comprised the following species:

| Abbreviation | Botanical name | Common name |
|---|---|---|
| AMARE | Amaranthus retroflexus L. | Pigweed |
| CASTO | Cassia tora L. | Sickle pod |
| CENCY | Centaurea cyanus L. | Cornflower |

When used at a rate of 0.5 kg a.i./ha in the post-emergence method, broad-leaved undesirable plants can be very readily controlled with the compounds 15.005 and 9.011.

Compared with structurally similar compounds of the prior art, for example EP-A-169 815, the novel compounds surprisingly have advantageous properties as shown by the results listed in Tables I and II below. The following sulfonylureas were used as comparative agents A and B:

| Abbreviation | Botanical name | Common name |
|---|---|---|
| TRZAW | Triticum aestivum | Winter wheat |
| ABUTH | Abutilon theophrasti | Velvetleaf |
| AMARE | Amaranthus retroflexus | Pigweed |
| CHEAL | Chenopodium album | Common lambsquarters |
| POLPE | Polygonum persicaria | Ladysthumb |
| SINAL | Sinapis alba | White mustard |

The following test plants were used:

| Abbreviation | Botanical name | Common name |
|---|---|---|
| TRZAW | Triticum aestivum | Winter wheat |
| ABUTH | Abutilon theophrasti | Velvetleaf |
| AMARE | Amaranthus retroflexus | Pigweed |
| CHEAL | Chenopodium album | Common lambsquarters |
| POLPE | Polygonum persicaria | Ladysthumb |
| SINAL | Sinapis alba | White mustard |

TABLE I

Comparison of results from greenhouse experiments using the post-emergence method

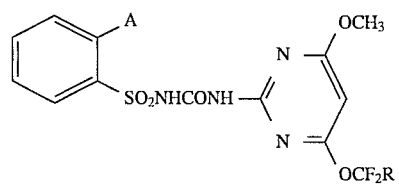

| Ex. No. | 9.011 | | A | |
|---|---|---|---|---|
| A | $NO_2$ | | $CO_2CH_3$ | |
| $(X)_m R^2$ | $OCH_3$ | | $OCHF_2$ | |
| R | F | | H | |
| Application rate (kg/ha a.i.) | 0.06 | 0.03 | 0.06 | 0.03 |
| Test plants Damage in % | | | | |
| TRZAW | 20 | 10 | 70 | 70 |
| ABUTH | 100 | 100 | 100 | 100 |
| AMARE | 100 | 100 | 100 | 100 |
| CHEAL | 100 | 100 | 100 | 100 |
| POLPE | 90 | 90 | 100 | 100 |
| SINAL | 95 | 95 | 95 | 95 |

TABLE II

Comparison of results from greenhouse experiments using the post-emergence method

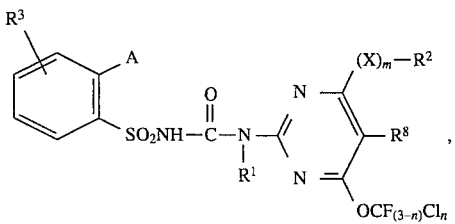

| Ex. No. | 9.011 | | B | |
|---|---|---|---|---|
| A | $NO_2$ | | $CO_2CH_3$ | |
| R | F | | Br | |
| Application rate (kg/ha a.i.) | 0.015 | 0.0075 | 0.015 | 0.0075 |
| Test plants Damage in % | | | | |
| TRZAW | 10 | 0 | 0 | 0 |
| ABUTH | 90 | 85 | 80 | 20 |
| AMARE | 100 | 100 | 50 | 50 |
| CHEAL | 90 | 90 | 50 | 30 |
| POLPE | 70 | 70 | 70 | 50 |
| SINAL | 95 | 90 | 80 | 80 |

We claim:

1. A substituted sulfonylurea of formula I

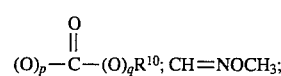

where n and m are each 0 or 1;

$R^1$ is hydrogen, $C_1$–$C_4$-alkyl, $C_3$–$C_6$-alkenyl or $C_3$–$C_6$-alkynyl;

$R^2$ is halogen or trifluoromethyl when m is 0 or $C_1$–$C_4$-alkyl, $C_3$–$C_6$-alkenyl or $C_3$–$C_6$-alkynyl when m is 1 or trifluoro- or chlorodifluoromethyl when X is O or S and m is 1;

X is O, S or N—$R^4$, where $R^4$ is hydrogen or $C_1$–$C_4$-alkyl;

$R^3$ is hydrogen, halogen, $C_1$–$C_4$-alkyl, $C_1$–$C_4$-haloalkyl, $C_1$–$C_4$-alkoxy or $C_1$–$C_4$-haloalkoxy;

A is $NO_2$, $NH_2$, OH, CN, SCN, $S(O)_\ell R^5$, $SO_2NR^6R^7$, a group $ER^7$, where E is O, S or $NR^9$, $(O)_p\!-\!\underset{\underset{O}{\|}}{C}\!-\!(O)_q R^{10}$; $CH{=}NOCH_3$;

$C_1$–$C_4$-alkyl which is unsubstituted or mono-, di- or trisubstituted by methoxy, ethoxy, $SO_2CH_3$, cyano, thiocyanato or $SCH_3$, or $C_2$–$C_4$-alkenyl which is unsubstituted or mono-, di- or trisubstituted by halogen, nitro or cyano;

$R^5$ is $C_1$–$C_6$-alkyl which may carry from one to three of the following radicals: halogen, $C_1$–$C_4$-alkoxy, $C_1$–$C_4$-haloalkoxy, $C_1$–$C_4$-alkoxy-$C_1$- or $C_2$-alkoxy, $C_3$–$C_7$-cycloalkyl and/or phenyl; $C_5$–$C_7$-cycloalkyl which may carry from one to three $C_1$–$C_4$-alkyl groups; $C_2$–$C_6$-alkenyl or $C_3$–$C_6$-alkynyl;

$R^6$ is hydrogen, $C_1$- or $C_2$-alkoxy or $C_1$–$C_6$-alkyl, or, together with $R^7$, forms a $C_4$–$C_6$-alkylene chain in which a methylene group may be replaced with an oxygen atom or a $C_1$–$C_4$-alkylimino group;

$R^7$ is $C_1$–$C_4$-alkyl, $C_2$–$C_4$-alkenyl or $C_3$- or $C_4$-alkynyl, it being possible for the stated radicals to carry a further one to four halogen or $C_1$–$C_4$-alkoxy radicals, or is $C_3$–$C_6$-cycloalkyl, or where E is $NR^9$, is furthermore methylsulfonyl, trifluoromethylsulfonyl, ethylsulfonyl, acetyl which may carry one to three halogen atoms, or methoxycarbonyl, dimethylcarbamoyl or dimethylsulfamoyl;

o is 0, 1 or 2;

p and q are 0 or 1, and, where p is 0, q is likewise 0, and $R^8$ is hydrogen or halogen;

$R^9$ is hydrogen, methyl or ethyl;

$R^{10}$ is $C_1$–$C_3$-alkyl, $C_1$–$C_3$-haloalkyl, $C_1$- or $C_2$-alkoxy-$C_1$- or $C_2$-alkyl, $C_2$–$C_4$-alkenyl, $C_3$–$C_6$-cycloalkyl or $C_2$- or $C_3$-haloalkenyl, or, where p is 1 and q is 0, is furthermore $C_1$–$C_3$-alkylamino or di-($C_1$- or $C_2$-alkyl)-amino, and environmentally compatible salts thereof.

2. A sulfonylurea of the formula I as defined in claim 1, where $R^1$ is hydrogen or methyl;

$R^2$ is halogen or trifluoromethyl, when m is 0 and methyl when m is 1;

X is O or NH;

$R^3$ is hydrogen, halogen, methyl or methoxy;

A is $NO_2$, $N[CH_3]SO_2CH_3$, a group $SO_2R^5$, where $R^5$ is $C_1$–$C_4$-alkyl, a group $SO_2NR^6R^7$, where $R^6$ and $R^7$ are each methyl, or an $OR^7$ group, where $R^7$ is $C_1$–$C_2$-alkyl which may carry from one to three or four halogen atoms or one methoxy group;

and $R^8$ is hydrogen, and environmentally compatible salts thereof.

3. A herbicidal composition comprising a sulfonylurea of the formula I as defined in claim 1 or a salt and carriers conventionally used for this purpose.

4. A method for controlling undesirable plant growth, wherein an effective amount of a sulfonylurea of the formula I as defined in claim 1 or one of its salts is allowed to act, in a herbicidally effective amount, on the plants or their habitat.

5. A sulfonylurea of the formula I as defined in claim 1, wherein $R^1$ is hydrogen, X is O, $R^2$ is $CH_3$, N is 0, A is $NO_2$ and R is F.

6. A method for controlling undesirable plant growth, wherein an effective amount of a sulfonylurea of the formula I as defined in claim 5 or one of its salts is allowed to act in a herbicidally effective amount, on the plants or their habitat.

* * * * *

UNITED STATES PATENT AND TRADEMARK OFFICE
CERTIFICATE OF CORRECTION

PATENT NO.: 5,591,694

DATED: January 7, 1997

INVENTOR(S): HAMPRECHT et al.

It is certified that error appears in the above-identified patent and that said Letters Patent is hereby corrected as shown below:

On the cover page, item [22], the PCT filing date
"Sep. 25, 1992" should be --Aug. 25, 1992--.

Signed and Sealed this

Twenty-fifth Day of March, 1997

Attest:

BRUCE LEHMAN

*Attesting Officer*  *Commissioner of Patents and Trademarks*